(12) United States Patent
Dobbie

(10) Patent No.: US 7,906,139 B2
(45) Date of Patent: Mar. 15, 2011

(54) COMPOSITIONS AND METHODS OF USING LAMELLAR BODIES FOR THERAPEUTIC PURPOSES

(75) Inventor: James Dobbie, Lanarkshire (GB)

(73) Assignee: Lamellar Therapeutics Limited, Glasgow (GB)

( * ) Notice: Subject to any disclaimer, the term of this patent is extended or adjusted under 35 U.S.C. 154(b) by 1175 days.

(21) Appl. No.: 10/678,743

(22) Filed: Oct. 3, 2003

(65) Prior Publication Data

US 2004/0126420 A1 Jul. 1, 2004

Related U.S. Application Data

(63) Continuation-in-part of application No. PCT/GB03/01451, filed on Apr. 2, 2003.

(51) Int. Cl.
*A61K 9/127* (2006.01)
(52) U.S. Cl. ........................................ 424/450
(58) Field of Classification Search .................. 424/450
See application file for complete search history.

(56) References Cited

U.S. PATENT DOCUMENTS

| | | | |
|---|---|---|---|
| 5,403,592 | A | 4/1995 | Hills |
| 5,462,752 | A | 10/1995 | Chao et al. |
| 5,925,375 | A | 7/1999 | Lenk et al. |

FOREIGN PATENT DOCUMENTS

| | | |
|---|---|---|
| GB | 2 335 853 | 10/1999 |
| JP | 295933 | 5/1989 |
| WO | 89/01777 | 3/1989 |
| WO | 91/12026 | 8/1991 |
| WO | WO 91/12026 | 8/1991 |
| WO | 95/08986 | * 4/1995 |
| WO | 96/03136 | 2/1996 |
| WO | 97/13501 | 4/1997 |
| WO | 98/53800 | 12/1998 |
| WO | WO 98/53800 | 12/1998 |
| WO | 99/03481 | 1/1999 |
| WO | 99/51244 | 10/1999 |
| WO | 00/18371 | 4/2000 |
| WO | 00/69412 | 11/2000 |
| WO | 01/72277 | * 10/2001 |
| WO | 02/24162 | 3/2002 |
| WO | WO 02/24162 | 3/2002 |

OTHER PUBLICATIONS

Cevc (1993) Phospholipids Handbook, New York: Marcel Dekker, Inc.
Dobbie, et al. (1996) Ultrastructure, distribution and density of Lamellar bodies in human peritoneum. Perit Dial Int. 16, 482-487.
Hite (2002) Surfactant deficiency in adults. Clini Pulm Med, 9(1), 39-45.

* cited by examiner

*Primary Examiner* — Gollamudi S Kishore
(74) *Attorney, Agent, or Firm* — Klauber & Jackson LLC

(57) ABSTRACT

Compositions comprising lamellar bodies for removal of extra and intra-vascular fibrin for therapeutic purposes are disclosed. These lamellar compositions are also useful in surgical procedures wherein formation of post-surgical adhesions are likely. Methods of preventing and/or modifying fibrin clots and treating and/or preventing adhesions by administering a therapeutically effective amount of a composition to a patient requiring such treatment are also disclosed.

14 Claims, 24 Drawing Sheets

A

B

C

D

FUSED SYNTHETIC
LAMELLAR BODIES &

COMPOSITIONS AND METHODS OF USING LAMELLAR BODIES FOR THERAPEUTIC PURPOSES

CROSS-REFERENCE TO RELATED APPLICATIONS

The present application is a Continuation-in-Part application claiming the priority of copending PCT/GB03/001451, filed on Apr. 2, 2003 which claims priority to UK application No. GB0207653.7, filed on Apr. 3, 2002, the disclosures of which are incorporated by reference herein in their entireties. Applicants claim the benefit of this application under 35 U.S.C. §119 (a-d).

FIELD OF THE INVENTION

This invention relates to phospholipid constructs which act as surrogate lamellar bodies in body cavities, blood vessels, ducts and tissues to modify the deposition and removal of extra and intra-vascular fibrin for therapeutic purposes. The invention further relates to compositions and methods of treatment using these constructs. In addition, the invention relates to compositions and methods for preventing post-operative adhesions by administration of synthetic or naturally occurring lamellar bodies, or treating patients having adhesions resulting from a surgical procedure.

BACKGROUND OF THE INVENTION

Many animals possess a coelomic cavity which separates the gut from other structures. Peritoneum, like pleura and pericardium, is a derivative of the coelomic cavity. In the most primitive of animals, consisting only of a cylindrical body wall containing a tubular gut, separation of the two parts by a non-stick derivative of the coelomic cavity is essential if peristalsis is to maintain a flow of nutrition from one end of the gut to the other. Abolition of peristalsis through adhesion of gut to body wall is incompatible with life, thus from the earliest of evolutionary time, provision of a non-stick surface between these vital structures has been imperative. In man, peritoneal adhesions resulting from any cause, whether due to surgery, chronic organismal inflammation or endometriosis, expose the individual to dire consequences.

In primitive animals, the coelomic cavity is under constant and serious threat from ingress of organisms or noxious molecules from the external environment, either through the gut or body wall. The danger to life is rapid, as is the unobstructed spread of an invader throughout the entire coelom. Thus, an immediate defensive response evolved whereby the cavity fluid thickens to prevent leakage and entrap invading organisms. This event is achieved by polymerization of a soluble protein (proto-fibrinogen) into a voluminous network. Medical science and biology in general remain largely ignorant of the primordial site and purpose of the elaborate and now highly evolved mechanism of clotting in the vascular systems of higher vertebrates. This has resulted in a failure to perceive that this system of clotting evolved in tandem with another equally life maintaining system of non-stick properties of the lining surfaces of the coelomic cavity, which is the recently discovered lamellar bodies secretory system. The vast bulk of research into the clotting mechanism is almost entirely vasculo-centric and hitherto lack of research into the clotting mechanism in serous cavities has resulted in failure to recognize the crucial role of the lamellar body system in the gelation of fibrin throughout the entire body.

Post Operative Surgical Adhesions

It is widely recognized in the surgical community that peritoneal adhesions are an extremely common complication of abdominal and pelvic surgery, giving rise to significant morbidity, mortality and unwanted loss of operating time and expense to health services throughout the world. However, until recently, lack of good epidemiological data, combined with an inability to effectively prevent adhesion formation, has limited the impetus to carry out serious investigation of this disorder.

In the developed world, the most common cause of peritoneal adhesions is abdominal surgery, where the main cause of small bowel obstruction is adhesion formation following previous surgery. Indeed, throughout this century there has been a continual rise in the cases of intestinal obstruction due to adhesions, from 7% in 1930 to 64% in 1969, which reflects the increasing frequency of abdominal surgery in the population at large. It is now recognized that adhesions are responsible for a significant morbidity, loss of work and expense to health services world-wide. With the recent development of minimally invasive surgery, it was hoped that adhesions would be a thing of the past. However, this has not been the case.

A recent epidemiological study has provided accurate and detailed statistics on the incidents of adhesions, giving evidence of the seriousness of the problem. This study was carried out by the Surgical and Clinical Adhesions Research (SCAR) Group using validated data from the Scottish National Health Service medical record linkage database. It identified patients undergoing abdominal or pelvic surgery in 1986 who had no record of surgery in the preceding five years. Patients were then followed for ten years and subsequent re-admissions were reviewed and outcomes classified by the degree of adhesion. 5.7% of all re-admissions were classified as being caused incontrovertibly by adhesions. A further 28.9% were readmitted with signs and symptoms of subacute obstruction believed to be most probably caused by adhesions. In Scotland in 1994, a total of 4,199 admissions for a population of 5 million were directly related to adhesions. (Ellis H, Moran B J, Thompson J N et al. Adhesion-related hospital re-admissions after abdominal and pelvic surgery: A retrospective cohort study. Lancet. 1999;353;1476-1480). These figures highlight a remarkable scale of adhesion related admissions, when compared to similar figures of other common, essential surgical procedures, such as hip replacement operations (4,394), coronary artery bypass grafts (4,020) or haemorrhoid surgery (4,226) during the same time period and the same population.

A further effect of adhesions is the difficulty and time taken to dissect them before proceeding with an operation. A study of workload involved for 120 patients undergoing a re-operative laparotomy estimated a mean increase of 24 minutes in the total time of the operation because of intra abdominal adhesions from previous surgery. There is also an intra operative danger of adhesiolysis (lysis of adhesions), as was demonstrated in 274 patients undergoing re-laparotomy where a 21% risk of bowel perforation was identified.

With respect to mortality, intestinal obstruction is the most severe consequence of adhesions. It has been shown that of patients who require abdominal re-operation, 30% to 41% have adhesion related intestinal obstruction.

It should be noted that the clinical consequences of adhesions are not simply confined to the gut. Adhesions are the leading cause of secondary infertility in women, and are responsible for substantial abdominal and pelvic pain and discomfort.

In fact, surgical adhesions are known to cause problems in a range of areas. The following types of surgery can result in surgical adhesions, which cause a number of problems; abdominal, thoracic (including both cardiac and pleural), spinal, intra-cranial, intra-ventricular, intra-placental, urological including both gynecological and fertility which can occur during fallopian tube surgery, urinary tract surgery, IVF treatment and during reversal surgery in the vas deferens), orthopedics, arthroscopy, ear, nose and throat, neurological (including peripheral nerve surgery and spinal microsurgery), cardiology and radiology.

The incidence of post-operative adhesions is becoming increasingly unacceptable to healthcare communities throughout the world. However, recent advances in the molecular biology of serous cavities have at last provided accurate information on the aetiopathogenesis of adhesions, which allows evidence based strategies for their prevention during any surgical procedure in any of the derivatives of the coelomic cavity. These new preventative measures involve an understanding of the formation and removal of fibrin in serous cavities. Current knowledge presumes that the only factors are molecular and cellular elements involved in fibrin gelation and fibrinolysis. In the current invention it can be seen that the secretion of lamellar bodies plays a key role in both the physical structure of fibrin deposition and the speed and extent of its removal. The current invention utilizes this knowledge to provide therapeutic uses of lamellar body solutions.

The Role of Fibrin in the Acute Inflammatory Response

Fibrinogen is an acute phase, soluble protein, which increases in the blood and tissue fluids temporarily as a consequence of inflammatory reactions. Contact with pro-coagulant factors causes polymerization of fibrinogen to form a fibrinous gel.

At the beginning of the $20^{th}$ Century, pathologists described and defined the sequence of events in the acute inflammatory response. The reactive changes involved three sequential processes:
1. changes in vascular caliber and blood flow
2. increased vascular permeability and the formation of protein rich inflammatory exudate
3. escape of leucocytes from vessels into extravascular tissue spaces An initial event in the tissue spaces is the appearance of fibrin identified by a variety of histochemical techniques. Early histological studies recognized that fibrin represented an attempt to wall-off the infected or damaged area, as well as providing a "scaffolding" of fibers in the turgid edematous tissue to assist the amoeboid movement of inwardly migrating leucocytes. When looking at acute inflammatory response, an early and orderly disappearance of fibrin heralded a successful outcome to the inflammatory response, as the excess tissue fluid drained away into the lymphatics and the fibrin scaffolding was dismantled.

Thus, the optimal result of an acute inflammatory response is complete restitution of the normal structure and function of the affected tissue. This process is referred to as resolution or healing by first intention. In the process of resolution, the primary task is the removal of cellular debris and fibrin. If, however, heavy deposits of fibrin are formed during the early stages of acute inflammation, they may not be removed completely within a few days by the fibrinolytic enzymes of the inflammatory exudate. The consequence of this failure can be profound, as fibrin which is not rapidly removed undergoes a process called organization. Macrophages migrate into the fibrin, closely followed by ingrowth of new capillaries and fibroblasts to form a tissue known as granulation tissue. As granulation tissue matures, it is eventually replaced by a firm, dense, fibrous tissue more commonly referred to as scar tissue. Where granulation tissue between two opposing tissue surfaces or organs is transformed by this process, the dense fibrous tissue joining the previously separate entities is referred to as an adhesion. This process is also known as healing by second intention and the adhesions may seriously compromise normal function at the site of the original acute inflammatory response.

In the pre-antibiotic era, the clinical signs and symptoms of fibrinous exudates in response to bacterial infections formed the bulk of everyday medical practice. The sound of a friction rub heard on auscultation of the chest signified a thick fibrinous exudate, the acute inflammatory response of the pleura to underlying pulmonary infection, as in pneumococcal pneumonia. Pericardial friction rubs were also commonplace, not only in response to diverse infections, but also in uremia and rheumatic fever. With the complete disappearance of many disease types as medicine advanced, the previously recognized role of fibrinous deposition in most diseased states was not appreciated by the current generation of researchers. An exception to this rule has been molecular biologists working in the field of rheumatoid disorders, where the grossly incapacitating effect of conversion of extravascular fibrin deposits to dense fibrous tissue remains a focus of ongoing research.

Also, this type of post-inflammatory adhesion can be seen in peritonitis, pericarditis, joint disease (for example in cases of post-rheumatoid arthritis and severe gout), CNS disease (including meningitis), ear, nose and throat diseases, gynecological disease (such a chlamydia which attracts fibrin deposition) and urology.

In the last two decades there has been considerable advances in the molecular biology of mesothelium, its reaction to injury and inflammation and its repair and regeneration. A thin mesothelial monolayer resting on a basement membrane covers all of the abdominal organs (visceral) and the wall of the abdominal cavity (parietal). In an adult, its surface measures up to $2\ m^2$, presenting a large area which acts as a semi-permeable membrane for the exchange of water and small molecular weight solutes. The human peritoneal cavity exists in normal life as a potential space with the opposing surfaces being separated by only $5\mu$. It therefore contains no more than 50 ml of clear, sterile fluid with a low specific gravity and low protein content. Fibrinogen is not present and therefore serous fluid will not clot.

The local inflammatory response of the peritoneum is similar to other tissues, but the peritoneal lining is unique in that it presents a large exudative and absorptive surface. The lining can separate to accommodate many liters of fluid. At sites of irritation there is an outpouring into the peritoneal cavity of fluid with a high protein content. This exudate contains fibrinogen which polymerizes to solid fibrin on contact with local tissue factor released by mesothelium or leucocytes. Plaques of fibrinous exudate forming on the inflamed surface glue adjacent bowel, mesentery and omentum to each other. The process of adhesion is greatly facilitated by the inhibition of peristalsis which allows loops of bowel and omentum to lie undisturbed while the highly adhesive fibrin progressively walls-off the damaged area. Although this process has evolved to localize infection and halt its spread through the entire peritoneal cavity, the same response inevitably occurs when the peritoneum is surgically opened under sterile conditions.

Thus, as part of the inflammatory response, the mesothelium has a powerful pro-coagulant ability through its local production of tissue factor. This, when released into the peritoneal exudate, initiates a cascade leading to the polymerization of fibrinogen to solid fibrin. This is balanced by an equally powerful fibrinolytic capability where normal peritoneal tissues contain measurable levels of plasminogen which can be converted to plasmin by the secretion of tissue plasminogen activator. These processes constitute cascade systems finely balanced by activators and inhibitors.

SUMMARY OF THE INVENTION

The present invention is based on the applicant's research, which has shown that the gelation of fibrin is profoundly affected when it occurs in an environment containing lamellar bodies. Furthermore, the applicant's current research indicates that lamellar bodies subserve surfactant, lubricant, water repellent and transport functions. In serous cavities, its major function would appear to be the highly efficient reduction of friction through self-lubricating ball and roller bearings which constantly form and reform between opposing surfaces.

It would be advantageous to provide for compositions and methods of preventing adhesions forming between surfaces during surgical procedures through use of the lamellar bodies of the present invention. Furthermore, it would also be advantageous to provide for compositions and methods of dissolving any blood clots and preventing coagulation through use of the lamellar bodies of the present invention.

Accordingly, a first aspect of the invention provides for lamellar bodies for use as an active therapeutic substance. In a preferred embodiment, the lamellar bodies may be used for the prevention of fibrin clot formation, for the modification of fibrin clots, for the prevention and/or treatment of adhesions, or for the prevention and/or modification of intravascular clots. In a yet further preferred embodiment, the lamellar bodies are provided in a solution, preferably as a spray, and may be provided for use in combination with hyaluronan and/or chondroitin sulphate B. The lamellar bodies may be synthetic or may be obtained from a natural source. A yet further preferred embodiment provides for a mixture of natural and synthetic lamellar bodies. Preferably the lamellar bodies are applied at 30 minute intervals and the dosage concentration of the lamellar bodies is $10 \times 10^9$ per ml. Preferably the lamellar bodies incorporate other active agents, such as, but not limited to, anti-estrogen or anti-tumor compounds.

A second aspect of the invention provides for a pharmaceutical composition comprising a therapeutically effective amount of lamellar bodies, and a pharmaceutically acceptable carrier and/or excipients. In a preferred embodiment, the pharmaceutical composition comprises lamellar bodies comprising about 44-60% phosphatidylcholine, about 15-23% sphingomyelin, about 6-10% phosphatidyl ethanolamine, about 2-6% phosphatidyl serine, about 2-4% phosphatidyl inositol and about 4-12% cholesterol by weight, and a pharmaceutically acceptable carrier. This composition may further comprise about 0-3% by weight of lysophosphatidyl choline. In a more preferred embodiment, the pharmaceutical composition comprises lamellar bodies comprising about 54% phosphatidylcholine, about 19% sphingomyelin, about 8% phosphatidyl ethanolamine, about 4% phosphatidyl serine, about 3% phosphatidyl inositol and about 10% cholesterol by weight, and a pharmaceutically acceptable carrier. This composition may further comprise about 2% by weight of lysophosphatidyl choline. Preferably the pharmaceutical composition may be used for the prevention of fibrin clot formation, for the modification of fibrin clots, for the prevention and/or treatment of adhesions, or for the prevention and/or modification of intravascular clots.

In a yet further preferred embodiment, the pharmaceutical composition comprising lamellar bodies is prepared as a solution, preferably as a spray, and may be provided for use in combination with hyaluronan and/or chondroitin sulphate B. The lamellar bodies in the composition may be synthetic or may be obtained from a natural source. A yet further embodiment provides for a composition containing a mixture of natural and synthetic lamellar bodies. Preferably the composition is applied at 30 minute intervals and the dosage concentration of the lamellar bodies in the composition is $10 \times 10^9$ per ml. Preferably the composition containing lamellar bodies incorporates other active agents, such as, but not limited to, anti-estrogen or anti-tumor compounds.

A third aspect of the invention provides for a method of preventing and/or modifying fibrin clots comprising administering to a patient requiring such treatment a therapeutically effective amount of lamellar bodies or pharmaceutical compositions comprising the lamellar bodies described herein. In one embodiment, the lamellar bodies or pharmaceutical compositions comprising lamellar bodies may be prepared as a solution. The composition may be used in combination with hyaluronan and/or chondroitin sulphate B. The lamellar bodies may be synthetic or derived from a natural source. The composition may be in the form of a spray. The composition may be prepared in a dosage form suitable for administration at 30 minute intervals with the lamellar bodies present in a concentration of about $10 \times 10^9$/ml. The composition may be prepared such that the lamellar bodies incorporate at least one other therapeutically active agent. The other agents may be, but are not limited to, at least one anti-estrogen compound or one chemotherapeutic anti-tumor compound. The administration may comprise a mixture of synthetic lamellar bodies or lamellar bodies obtained from a natural source.

A fourth aspect of the invention provides for a method of treating and/or preventing adhesions during surgery comprising administering a therapeutically effective amount of lamellar bodies or pharmaceutical compositions comprising the lamellar bodies described herein to a patient requiring such treatment. One preferred embodiment provides for a means of delivering the lamellar bodies or pharmaceutical compositions comprising the lamellar bodies using methods that can easily be implemented during surgery. Included in this embodiment are solutions that may be applied using spraying techniques. The composition may be used in combination with hyaluronan and/or chondroitin sulphate B. The lamellar bodies may be synthetic or derived from a natural source. The composition may be in the form of a spray. The composition may be prepared in a dosage form suitable for administration at 30 minute intervals with the lamellar bodies present in a concentration of about $10 \times 10^9$/ml. The composition may be prepared such that the lamellar bodies incorporate at least one other therapeutically active agent. The other agents may be, but are not limited to, at least one anti-estrogen compound or one chemotherapeutic anti-tumor compound. The administration may comprise a mixture of synthetic lamellar bodies or lamellar bodies obtained from a natural source.

A fifth aspect of the invention provides for a method of preventing and/or modifying intravascular clots comprising administering a therapeutically effective amount of lamellar bodies or pharmaceutical compositions comprising the lamellar bodies described herein to a patient requiring such treatment. One preferred embodiment provides for a method of dissolving blood clots, which are in the process of forming, or are formed and mature (ie. many days old). The composition may be used in combination with hyaluronan and/or chondroitin sulphate B. The lamellar bodies may be synthetic or derived from a natural source. The composition may be in the form of a spray. The composition may be prepared in a dosage form suitable for administration at 30 minute intervals with the lamellar bodies present in a concentration of about $10\times10^9$/ml. The composition may be prepared such that the lamellar bodies incorporate at least one other therapeutically active agent. The other agents may be, but are not limited to, at least one anti-estrogen compound or one chemotherapeutic anti-tumor compound. The administration may comprise a mixture of synthetic lamellar bodies or lamellar bodies obtained from a natural source. The administration may be by delivery of the lamellar bodies alone or in combination with other A sixth aspect of the invention provides for a method of preparing an agent for the prevention and/or modification of fibrin clots, wherein said method comprises the steps of:

a) preparing lamellar bodies from a mixture comprising about 44-60% phosphatidylcholine, about 15-23% sphingomyelin, about 6-10% phosphatidylethanolamine, about 2-6% phosphatidyl serine, about 2-4% phosphatidyl inositol, about 4-12% cholesterol by weight in saline; and b) adjusting the final concentration of the lamellar bodies prepared in Step a) to about $10\times10^9$/ml using saline, wherein said method results in preparation of an agent useful for the prevention and/or modification of fibrin clots.

A seventh aspect of the invention provides for a method of preparing an agent for the prevention and/or treatment of adhesions, wherein said method comprises the steps of:

a) preparing lamellar bodies from a mixture comprising about 44-60% phosphatidylcholine, about 15-23% sphingomyelin, about 6-10% phosphatidylethanolamine, about 2-6% phosphatidyl serine, about 2-4% phosphatidyl inositol, about 4-12% cholesterol by weight in saline; and b) adjusting the final concentration of the lamellar bodies prepared in Step a) to about $10\times10^9$/ml using saline, wherein said method results in preparation of an agent useful for the prevention and/or treatment of adhesions.

An eighth aspect of the invention provides for a method of preparing an agent for the prevention and/or modification of intravascular clots, wherein said method comprises the steps of:

a) preparing lamellar bodies from a mixture comprising about 44-60% phosphatidylcholine, about 15-23% sphingomyelin, about 6-10% phosphatidylethanolamine, about 2-6% phosphatidyl serine, about 2-4% phosphatidyl inositol, about 4-12% cholesterol by weight in saline; and b) adjusting the final concentration of the lamellar bodies prepared in Step a) to about $10\times10^9$/ml using saline, wherein said method results in preparation of an agent useful for the prevention and/or modification of intravascular clots.

In a preferred embodiment, the agents prepared as described above for the designated indications may be prepared as a pharmaceutical composition in a solution, preferably as a spray. The lamellar bodies so described may be synthetic or they may be naturally occurring. They may be used alone or in combination with hyaluronan or chondroitin sulphate. They may incorporate at least one other therapeutically active compound, such as an anti-estrogen or a chemotherapeutic anti-tumor compound. In a further preferred embodiment, they may be administered as a spray at 30 minute intervals at a concentration of $10\times10^9$/ml. They may be used during or after a surgical procedure. However, it is envisioned that other pharmaceutical compositions and formulations suitable for the given condition may be used. Suitable delivery systems may be encapsulation in microparticles or microcapsules. Methods of introduction can be enteral or parenteral and include but are not limited to intradermal, intramuscular, intraperitoneal, intravenous, subcutaneous, intranasal, epidural, topical and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent. In a specific embodiment, it may be desirable to administer the pharmaceutical compositions of the invention locally to the area in need of treatment, such as topical use on the skin; or to the surgical site directly by any suitable method known to the art.

A ninth aspect of the invention provides for a therapeutically effective amount of lamellar bodies for preparation of an agent, wherein the agent is used to treat Otitis media.

A tenth aspect of the invention provides for a method of treatment of Otitis Media.

In a preferred embodiment, the method of treating Otitis media comprises the steps of:
  a) introducing a composition including lamellar bodies into the middle ear; and
  b) allowing the lamellar bodies in the composition to modify the viscosity of the material in the middle ear, such that the material is capable of draining from the middle ear.

In another preferred embodiment, the method of treating Chronic Otitis Media (COM) comprises the steps of:
  a) inserting a fine needle through the tympanic membrane;
  b) introducing a composition, including lamellar bodies, through the fine needle into the middle ear; and
  c) allowing the lamellar bodies in the composition to modify the viscosity of the fibrin in the middle ear, such that it is capable of draining from the middle ear.

In yet another preferred embodiment, the method of treatment of Chronic Otitis Media (COM) comprises the steps of:
  a) making an incision in the tympanic membrane;
  b) introducing a composition, including lamellar bodies, through the incision into the middle ear;
  c) allowing the lamellar bodies in the composition to modify the viscosity of the fibrin in the middle ear;
  d) draining the modified fibrin from the middle ear through incision; and
  e) inserting a vent tube into the tympanic membrane to close the incision.

An eleventh aspect of the invention provides for a method of performing abdominal surgery.

In one preferred embodiment, the method for performing abdominal surgery comprises the steps of:
  a) applying a composition, including lamellar bodies, to at least part of the peritoneal lining of the abdominal cavity;
  b) allowing the composition to modify the tissue at the site of application; and
  c) removing the lamellar bodies post-surgically.

In another preferred embodiment, the method of performing abdominal surgery comprises the steps of:
  a) making an incision in the abdominal cavity in order to expose a surgical site;
  b) applying a composition, including lamellar bodies, to at least a part of the peritoneal lining of the abdominal cavity;

c) removing or modifying tissue at the surgical site; and
d) reclosing the abdominal cavity.

In yet another preferred embodiment, the method of performing abdominal surgery comprises the steps of:
a) making an incision in the abdominal cavity in order to expose a surgical site;
b) removing or modifying tissue at the surgical site;
c) applying a composition, including lamellar bodies, to at least part of the surgical site; and
d) reclosing the abdominal cavity.

According to a twelfth aspect of the present invention there is provided a use of lamellar bodies for the preparation of an agent for the prevention of fibrin clot formation. Alternatively there is provided use of lamellar bodies for the preparation of an agent for the modification of fibrin clots. In a preferred embodiment, the use is for the prevention of adhesions. In another preferred embodiment, the use is for the prevention of intravascular clots. In yet another preferred embodiment, the lamellar bodies are provided in solution. Preferably the lamellar bodies are provided in combination with any conventional pharmaceutical carrier or excipient. Preferably the lamellar bodies are provided in combination with hyaluronan and/or chondroitin sulphate B. Optionally the lamellar bodies are synthetic lamellar bodies. A further option is that the lamellar bodies are from a natural source. A yet further option is that a mixture of natural and synthetic lamellar bodies are used. In another preferred embodiment, the use of lamellar bodies is during surgical procedures. Preferably the lamellar bodies are sprayed onto the area to be treated. Preferably the lamellar bodies are applied at 30 minute intervals. Preferably the dosage concentration of the lamellar bodies is $10 \times 10^9$ per ml. Preferably the lamellar bodies incorporate other active agents. Preferably the lamellar bodies incorporate anti-estrogen compounds. Preferably the lamellar bodies may further incorporate chemotherapeutic anti-tumor agents.

According to a thirteenth aspect of the present invention there is provided a process for manufacturing a medicament intended for the prevention of fibrin clot formation, characterized in that lamellar bodies are used.

A fourteenth aspect of the invention provides a process for manufacturing a medicament intended for the modification of fibrin clots, characterized in that lamellar bodies are used.

Other advantages of the present invention will become apparent from the ensuing detailed description taken in conjunction with the following illustrative drawings.

BRIEF DESCRIPTION OF THE DRAWINGS

In order to provide a better understanding of the present invention, embodiments and uses of the invention will now be described by way of example only and with reference to the following Figures.

DETAILED DESCRIPTION OF THE INVENTION

Figure 1:
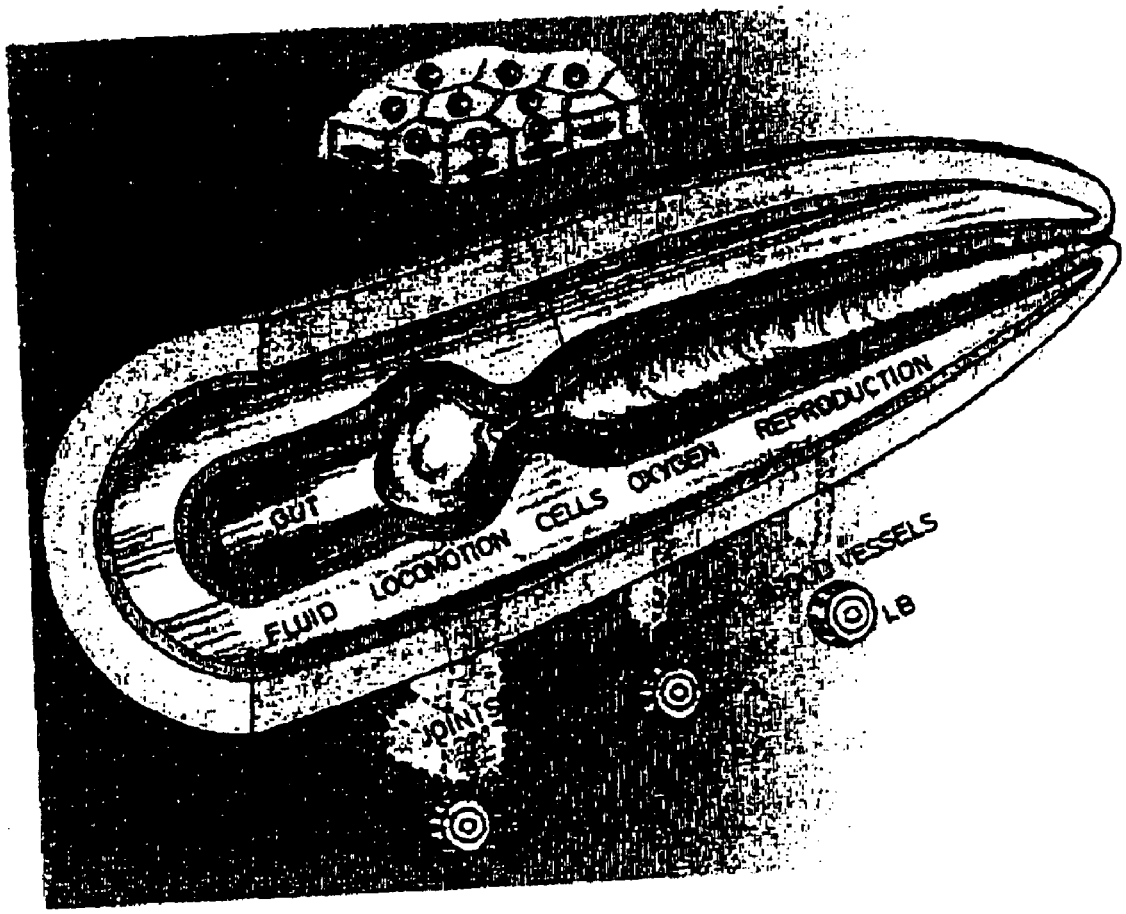
FIG. 1 is a diagrammatic representation of the primitive worm showing separation of the gut from the body wall by the coelomic cavity. The inherent non-stick property of the primordial coelom is believed to have been due to the secretion of lamellar bodies. This highly conserved system is perpetuated in the derivatives of the coelomic cavity in higher vertebrates in serous cavities, joints, ducts and blood vessels.
Figure 2:
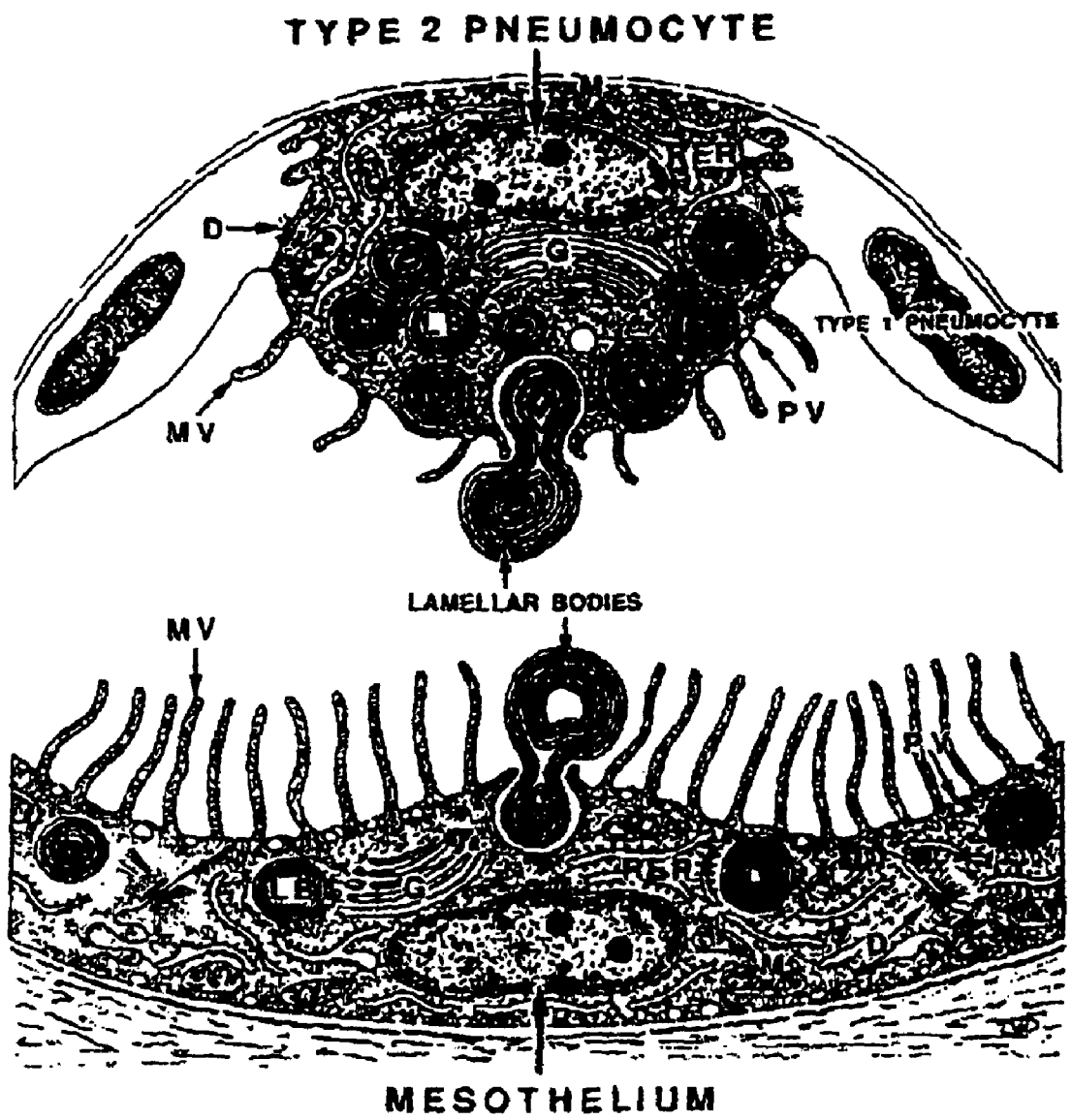
FIG. 2 is a diagrammatic representation of the appearance of the mesothelium and Type II pneumocytes demonstrating the close similarity of ultrastructural arrangements between cell types. Both cells bear microvilli (MB), while the cell surfaces are lined by micropinocytotic vesicles (PV). Well-developed junctional complexes contain desmosomes (D). Each cell type exhibits a cytoplasm well-endowed with mitochondria (M) and rough endoplasmic reticulum (RER). The Golgi apparatus (G) is prominent in both cells. Lamellar bodies (LB), consisting of whorls of alternate electron-dense and electron-lucent lamellae, are present throughout the cytoplasm in both cells and can be observed in the process of exocytotic extrusion from the apical surface (Dobbie J W. Am J Kid Dis. 1990;15:97-109).
Figure 3:
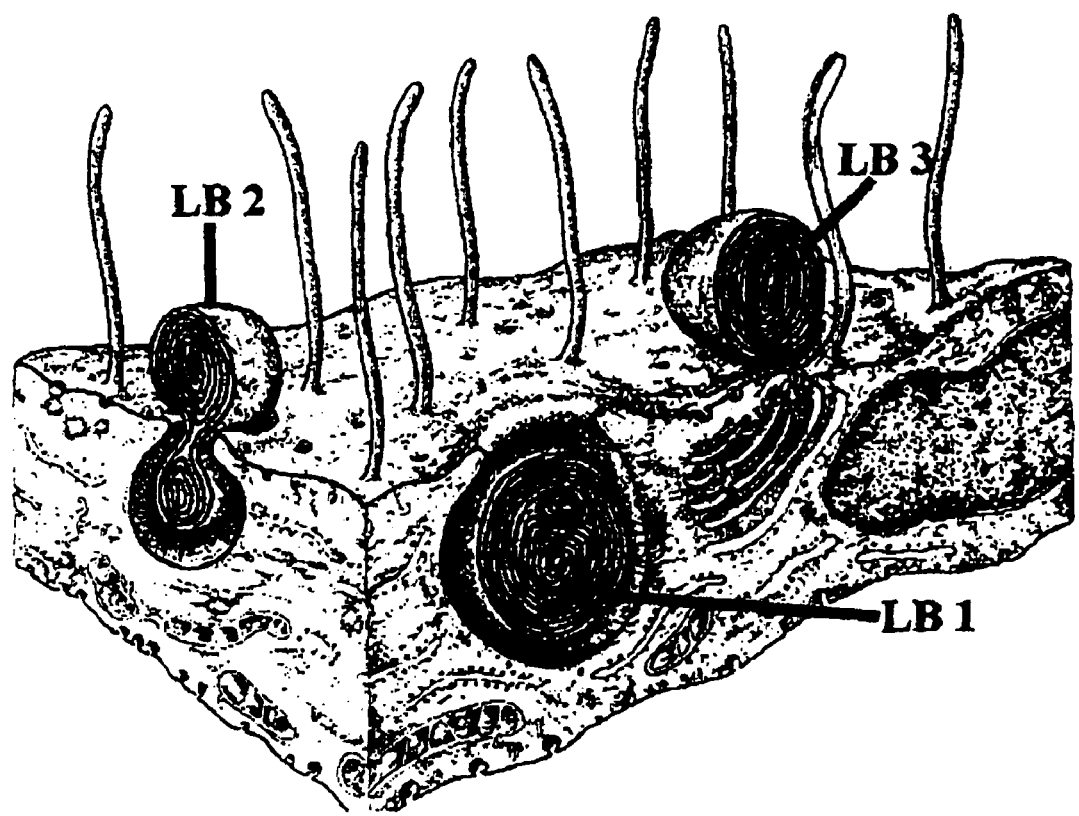
FIG. 3 is a diagrammatic representation based on serial sections of human parietal mesothelium illustrating the form and disposition of lamellar structures. LB2 is a full-formed body contained in the vesicle which is developing and opening to the cell surface. LB 1 is in the process of exocytotic extrusion through such an opening, while LB3 has been released onto the surface. The whorls, bifurcations and fingerprint patterns displayed in these diagrammatic cross-sections are representative of the lamellar geometry. Mesothelial-derived bodies share with their pulmonary counterparts. (Dobbie J W, Lloyd K J. Perit Dial Int. (1989); 9:215-219).

Before the present methods and treatment methodology are described, it is to be understood that this invention is not limited to particular methods, and experimental conditions described, as such methods and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" include one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference in their entirety.

Definitions

"Lamellar bodies or microbodies" as used throughout this document, refers to phospholipid, multilamellar, bilayered structures present in many tissues throughout the body, but also refers to the synthetic multilayered phospholipid structures having the novel composition described in the present invention. Thus, this term refers to both naturally occurring and synthetic lamellar bodies.

"Lamellasomes" as used herein refers to synthetically prepared lamellar bodies as described by the methods of the present invention.

"Adhesions" as used herein refers to fibrous bands of scar-like tissue that form between two surfaces inside the body. This abnormal union of bodily tissue can result in various disorders. For example, in the intestine, adhesions can cause partial or complete bowel obstruction. Intrauterine or pelvic adhesions can lead to infertility. In the eye, adhesions of the iris to the lens can lead to glaucoma. In the ear, adhesions can result in otitis media or chronic otitis media.

"Serous" as used herein refers to an exudate or effusion that is thin and watery, and which lacks a significant cellular component "Fibrin" is the product of an activated coagulation system. It forms in the extravascular space by cleavage of fibrinogen. It is an important component of a blood clot, as well as a thrombus. However, in the context of this section, it is important to understand that fibrin can be a prominent part of exudates that develop when vascular permeability/injury has been sufficiently great to allow a large molecule like fibrinogen to cross into the extravascular space. Fibrinogen is cleaved in the extravascular space to form fibrin.

Blood clots or "fibrin clots" are the clumps that result from coagulation of the blood. A blood clot that forms in a vessel or within the heart and remains there is called a thrombus. A thrombus that travels from the vessel or heart chamber where it formed to another location in the body is called an embolus, and the disorder, an embolism (for example, pulmonary embolism).

"Fibrinolysis" leads to the breakdown of fibrin clots) and is caused by the action of several enzymes. Fibrinolysis normally occurs continuously to keep naturally occurring blood clots from growing and causing problems. However, fibrinolysis can increase under certain conditions (such as intense exercise, inadequate oxygenation of tissues, or bacterial infections). Primary fibrinolysis refers to the normal breakdown of clots, whereas secondary fibrinolysis is the breakdown of blood clots and possible abnormal bleeding due to another medical disorder, medications, or other causes. In some situations, doctors may wish to speed up the rate of fibrinolysis. For example, when an abnormal "clot" forms in the blood vessels of the heart and results in a heart attack, man-made fibrinolytic enzymes (such as tPA, streptokinase, or Retavase) may be given to break up the culprit clot.

"Treatment" refers to therapy, prevention and prophylaxis and particularly refers to the administration of medicine or the performance of medical procedures with respect to a patient, for either prophylaxis (prevention) or to cure or reduce the extent of or likelihood of occurrence of the infirmity or malady or condition or event in the instance where the patient is afflicted.

A "therapeutically effective amount" is an amount sufficient to decrease or prevent the symptoms associated with the conditions or deficiencies contemplated for therapy with the compositions of the present invention.

"Slow release formulation" refers to a formulation designed to release a therapeutically effective amount of a drug or other active agent such as a polypeptide or a synthetic compound over an extended period of time, with the result being a reduction in the number of treatments necessary to achieve the desired therapeutic effect. In the matter of the present invention, a slow release formulation would decrease the number of treatments necessary to achieve the desired effect.

"Combination therapy" refers to the use of the agents of the present invention with other active agents or treatment modalities, in the manner of the present invention for treatment of otitis media or abdominal surgery. These other agents or treatments may include drugs such as corticosteroids, non-steroidal anti-inflammatory compounds, or other agents useful in treating or alleviating pain. The combined use of the agents of the present invention with these other therapies or treatment modalities may be concurrent, or the two treatments may be divided up such that the agent of the present invention may be given prior to or after the other therapy or treatment modality.

"Local administration" means direct administration by a non-systemic route at or in the vicinity of the site of an affliction, disorder, or perceived pain.

"Modify" means to alter the physical status of a material with respect to viscosity, adhesiveness and/or fluidity. In the present invention reference is made to "modification" of the fibrous gel, thus referring to changes in its physical characteristics, perhaps due to changes in hydration of the gel, although other factors may play a role in modification of the physical state.

"Acute otitis media" is an inflammation of the area behind the eardrum (tympanic membrane) in the chamber called the middle ear. Acute otitis media is an infection that produces pus, fluid, and inflammation within the middle ear. Acute otitis media frequently occurs as an aftereffect of respiratory infections as the nasal membranes and eustachian tube become swollen and congested.

"Chronic otitis media" refers to a middle ear infection that may develop when infection in the middle ear persists for more than 2 weeks. The middle ear and eardrum may start to sustain ongoing damage occasionally resulting in drainage through a nonhealing hole in the eardrum.

General Description

The present invention provides for compositions and methods of using isolated synthetic or naturally occurring lamellar bodies to prevent or modify fibrin clots, or to prevent, modify or dissolve existing intravascular clots. Moreover, the lamellar bodies or the compositions of the present invention comprising lamellar bodies can be used effectively to prevent adhesions following surgical procedures, including abdominal, thoracic (including both cardiac and pleural), spinal, intra-cranial, intra-ventricular, intra-placental, urological (including both gynecological and fertility which can occur during fallopian tube surgery, urinary tract surgery, IVF treatment and during reversal surgery in the vas deferens), orthopedics, arthroscopy, ear nose and throat, neurological (including peripheral nerve surgery and spinal microsurgery), cardiology and radiology.

Also, post-inflammatory adhesions can also be seen in peritonitis, pericarditis, joint disease (for example in cases of post-rheumatoid arthritis and severe gout), CNS disease (including meningitis), ear, nose and throat diseases, gynecological disease (such a chlamydia which attracts fibrin deposition) and urology. The lamellar bodies and compositions comprising lamellar bodies may be effective in treating these conditions as well.

Accordingly, the present invention provides for pharmaceutical compositions comprising a therapeutically effective amount of lamellar bodies and a pharmaceutically acceptable carrier and/or excipients. In one preferred embodiment, the pharmaceutical composition comprises about 44-60% phosphatidylcholine, about 15-23% sphingomyelin, about 6-10% phosphatidyl ethanolamine, about 2-6% phosphatidyl serine, about 2-4% phosphatidyl inositol and about 4-12% cholesterol by weight, and a pharmaceutically acceptable carrier. This composition may further comprise about 0-3% by weight of lysophosphatidyl choline.

In a most preferred embodiment, the pharmaceutical composition comprises a therapeutically effective amount of lamellar bodies, wherein said lamellar bodies comprise about 54% phosphatidylcholine, about 19% sphingomyelin, about 8% phosphatidyl ethanolamine, about 4% phosphatidyl serine, about 3% phosphatidyl inositol and about 10% cholesterol by weight, and a pharmaceutically acceptable carrier. This composition may further comprise about 2% by weight of lysophosphatidyl choline.

The present application accordingly provides for a method of preventing and/or modifying fibrin clots comprising administering a therapeutically effective amount of the above-noted compositions to a patient requiring such treatment. Also contemplated is a method of treating and/or preventing adhesions comprising administering a therapeutically effective amount of the above-noted lamellar bodies or compositions comprising lamellar bodies to a patient during surgery or to a patient having adhesions which formed subsequent to a surgical procedure. Furthermore, methods for preventing and/or modifying intravascular clots comprising administering a therapeutically effective amount of a composition to a patient requiring such treatment is also envisioned.

Lamellar bodies are a late discovery in modern biology, with their ultrastructural identification and association with the important function of pulmonary secretion of surfactant occurring in 1977 (Kalina M, Pease D C. The preservation of ultrastructure in saturated phosphatidylcholines by tannic acid in model systems and Type II pneumocytes. J. Cell Biol. 1977;74:726-741). Thus, the presence of lamellar bodies within Type II pneumocytes remained undetected until lung tissue, when fixed in an esoteric mixture of glutaraldehyde and tannic acid, revealed that the vacuoles were not empty, but in fact contained striking geometric configurations of densely osmophilic, closely packed lamellae. Now intracellular formation of phospholipid lamellae, their vacuole storage as mature lamellar bodies and the exocytotic release from the lumenal surface of Type II pneumocytes as pulmonary surfactant has been firmly established.

To this day, it is widely believed that the lubricant quality of the sparse fluid present in the peritoneal cavity is solely due to a low concentration of glycoso-aminoglycans which diffuses passively from underlying capillaries into the cavity. Due to the poor resolution of the light microscope, the mesothelial cell was for long believed to be a simple passive lining cell. The first electron microscopic study of the human peritoneum revealed the mesothelial cell to be of sophisticated sub-cellular content with a distinctive secretory organisation. Following the observation of the close ultrastructural concordance between mesothelial cells and Type II pneumocytes, studies showed that mesothelium synthesised phosphatidylcholine, the principle constituent of pulmonary surfactant, in amounts equal to those produced by the lung. Subsequently, when specialized fixation techniques developed for the preservation of lamellar bodies were applied to peritoneum, identical structures were found in each and every mesothelial cell. Originally believed to be exclusive to pulmonary alveoli, it was soon established that exocytotic secretion of lamellar bodies in association with surfactant protein A is a wide spread biological system located in the mesothelial lining of all serous cavities and present at a lower density in a variety of other tissues throughout the body. (Dobbie J W. Ultrastructural similarities between mesothelium and Type II pneumocytes and their relevance to phospholipids surfactant production by the peritoneum In: Khanna R, Nolph K D, Prowant B, Eds: Advances in Continuous Ambulatory Peritoneal Dialysis. University of Toronto Press, Toronto, 1988, pp 32-41. Dobbie J W, Pavlina T, Lloyd J, Johnson R C. Phosphatidylcholine synthesis by peritoneal mesothelium: Its implication for peritoneal dialysis. AM J Kid Dis. 1988;12: 31-36. Dobbie J W, Lloyd J K. Mesothelium secretes lamellar bodies in a similar manner to Type II pneumocyte secretion of surfactant. Perit Dial Int. 1989;9:215-221. Dobbie J W, Anderson J D. Ultrastructure, distribution and density of lamellar bodies in human peritoneum. Perit Dial Int. 1966; 16:482-87. Dobbie J W. Nature and disposition of intracavity and intramembranous phospholipids surface-active material and its role in peritoneal dialysis. Perid Dial Int. 1998;18:151-54. Dobbie J W. Surfactant protein A and lamellar bodies. A homologous secretory function of peritoneum, synovium and lung. Perit Dial Int. 1996;16:574-81. Dobbie J W, Tasiaux N, Meijers P et al. Lamellar bodies in synoviocytes, mesothelium and specific epithelia as possible site of auto-antigen in rheumatoid disease. Br J Theum. 1994;33:508-19. Dobbie J W, Hind C, Meihers P et al. Lamellar body secretion: Ultrastructural analysis of an unexplored function of synoviocytes. Br J Theum. 1995;34:13-23).

Figure 4:
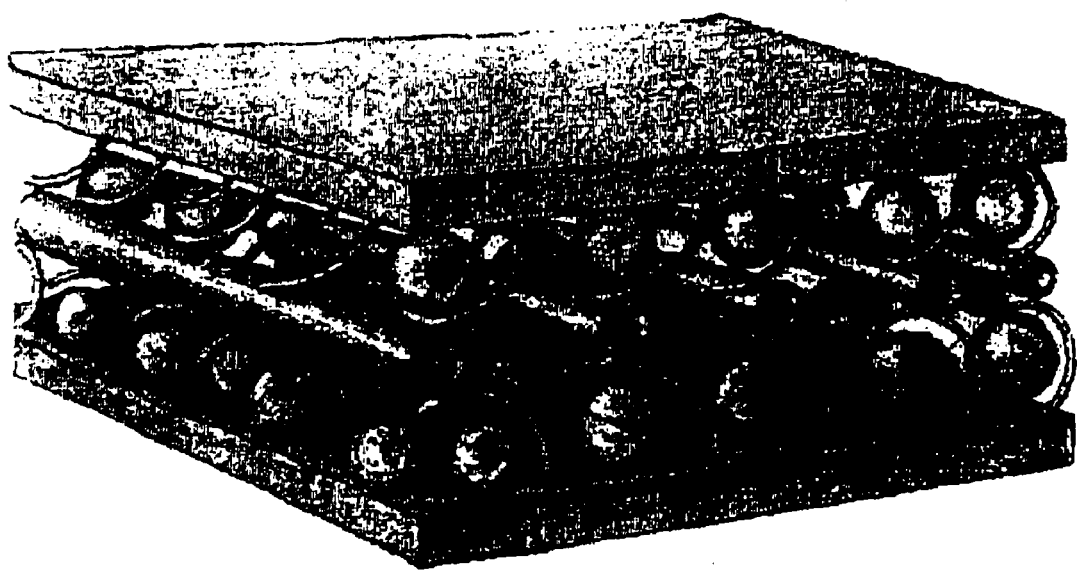
FIG. 4 is a diagrammatic representation based on three dimensional reconstruction of serial electron micrographs of normal human peritoneal mesothelium fixed in freshly prepared tannic acid, glutaraldehyde mixture to preserve phospholipid bi-layers. Enmeshed in the opposing microville, the lamellar bodies are arranged as microscopic spheres and cylinders. Where in vivo in the undisturbed state, it is presumed that lamellar bodies surrounded by and containing serous fluid, function as constantly changing ball and roller bearings and represent the mechanical mode of lubrication for all serous surfaces.
Figure 5:
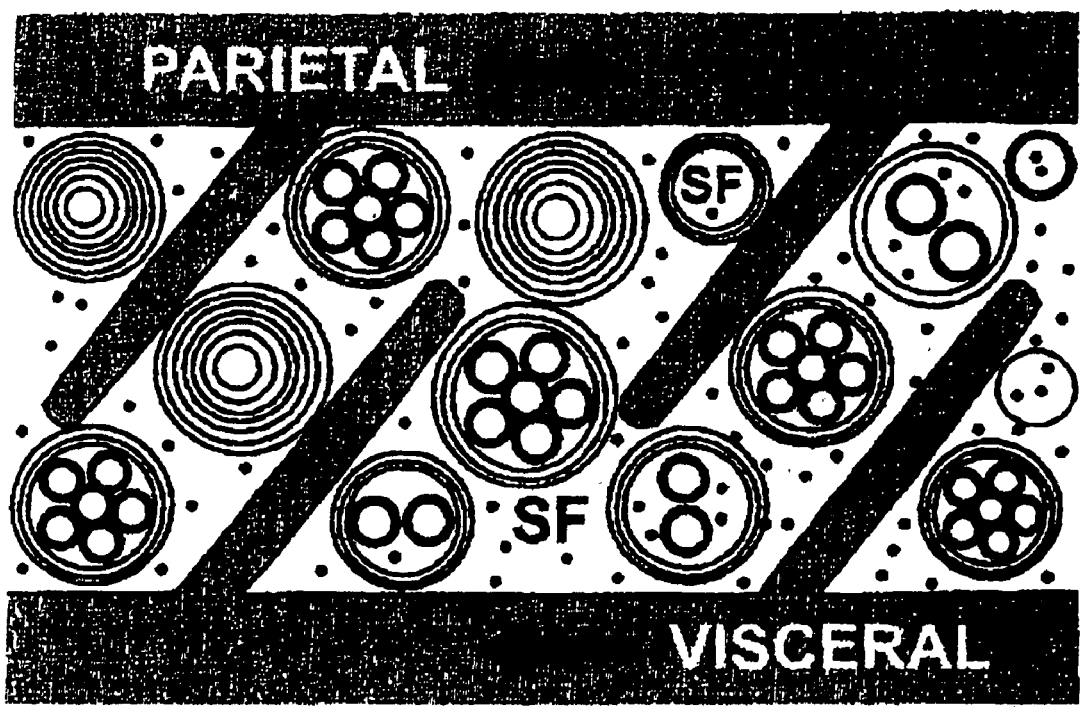
FIG. 5 is a simplified diagram based on the three-dimensional reconstructions illustrated in FIG. 4, showing the mechanics of the lamellar body lubricating system. The closely applied mesothelial layers, parietal and visceral, have interdigitating microville. The interstices are occupied by a thin film of serous fluie (SF) containing lamellar bodies shown here in cross section. This provides a lubricating system with a very low coefficient of friction. The ball and roller bearings have an internal organization of smaller ball and roller bearings. It is calculated that lateral movement causes a constant mixing and merging of the highly plastic phospholipid bilayers.
Figure 6:
FIGS. 6A-D show a selection of transmission electron micrographs demonstrating that the ultrastructural geometry of lamellar bodies from different sites are identical to that of synthetic lamellar bodies: A: Electron micrograph showing lamellar body in a human Type II pneumocyte. Magnification×155,000. B: Electron micrograph of lamellar body lying close to the surface of a human peritoneal mesothelial cell. Magnification×140,000. C: Electron micrograph of lamellar body in human Type B synoviocyte. Magnification×130,000. D: Electron micrograph of a synthetic lamellar body. Magnification×180,000.
Figure 6:
Figure 6C:
Figure 6D:
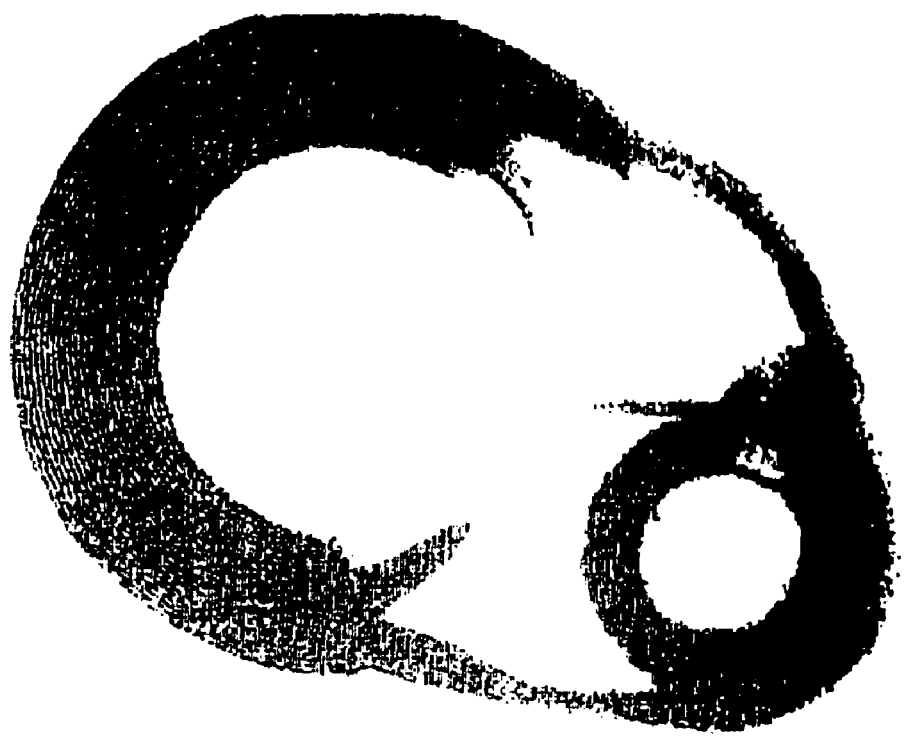
Figure 7:
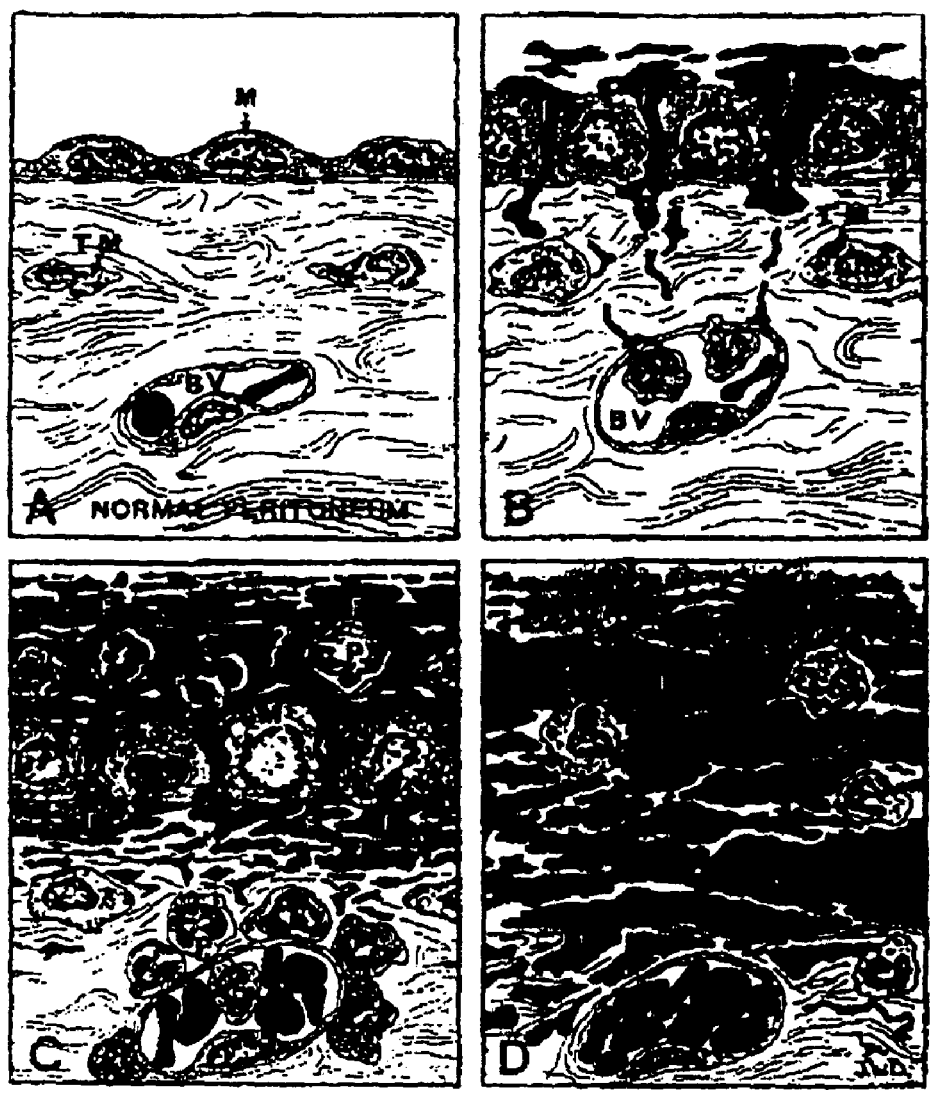
FIG. 7 is a diagrammatic representation of the sequential histopathological changes seen in the development of an acute inflammatory response in the peritoneum. In the initial stages (B), margination of esosinophils seen in the serosal blood vessels (BV) which leak fibrin (F). Tissue macrophages™ become swollen, while the mesothelial cells (M) assume a duboidal shape as fibrin seeps between them. As the inflammation continues (C), the mesothelial cells are progressively surrounded by fibrin. Eventually the mesothelial cells disappear (D) and the peritoneum is transformed into a tissue insudated with stratified layers of fibrin containing acute inflammatory cells (P). Dobbie J W. Perit Dial Int. 1988;8:241-248.
Figure 8:
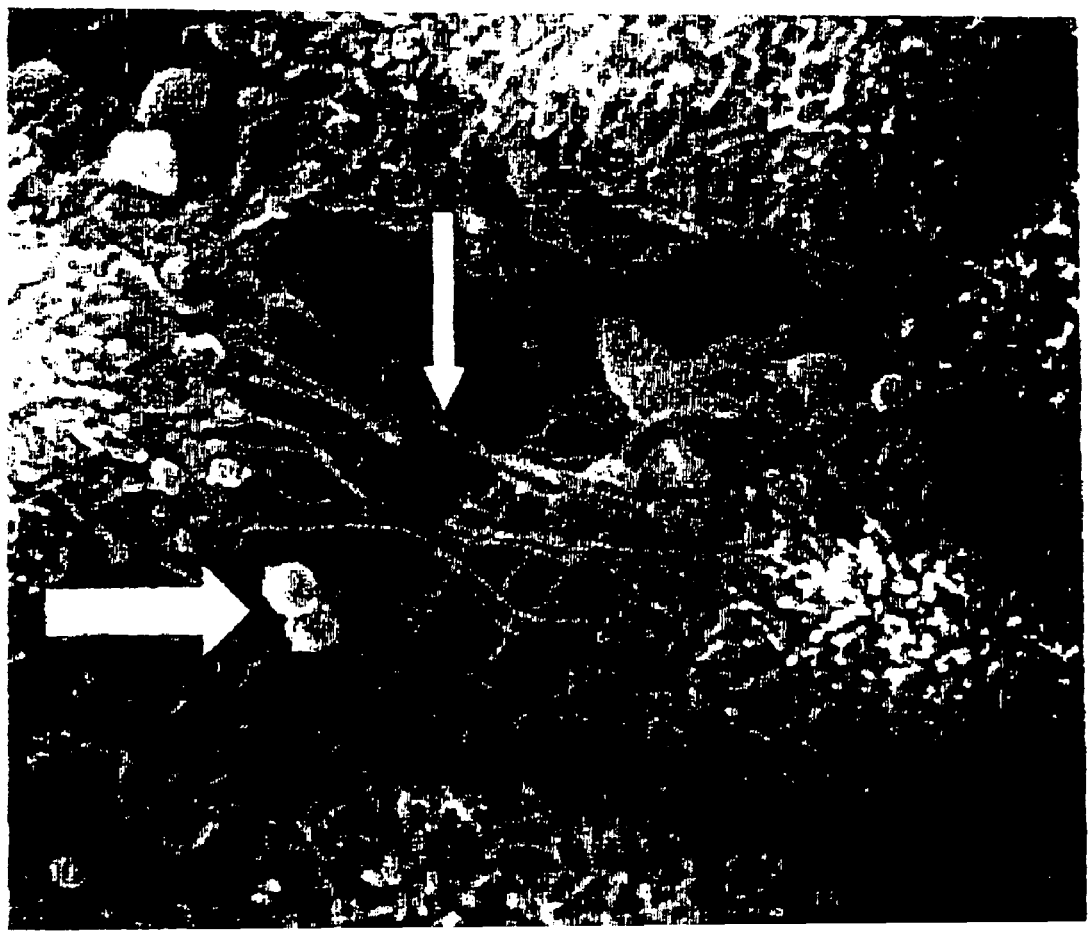
FIG. 8 is a scanning electron micrograph showing an association between fibrin fibers and lamellar bodies in an experimentally inflamed peritoneum. This scanning electron micrograph shows the mesothelial surface of a rat diaphragm from an experimental animal which had received daily intraperitoneal injections of small volumes of hypertonic peritoneal dialysate. This procedure stimulates minimal effusion of fibrin between mesothelial cells. The micrograph demonstrates lamellar bodies (LB thick arrow) in association with or adherent to strands of fibrin (thin arrow). Mag×10,500.
Figure 9:
FIG. 9 is a scanning electron micrograph showing early fibrin exudation in human peritoneal biopsy. This scanning electron micrograph is of the surface of a parietal peritoneal biopsy (human) obtained intra-operatively following procedures involving minimal handling of the viscera. There is a thin surface deposit of fibrin (arrows) enmeshed with a few red blood cells overlying an area of mesothelial damage and denudation. This illustrates the vulnerability of the delicate mesothelial monolayer to the effects of air-drying, and the micro-trauma of scuffing of the peritoneal surface, manually, by swabs and instruments which responds by exudation of fibrin. This represents the initial step in a process which may lead to adhesions. The dome-shaped outlines of normal individual mesothelial cells covered by microville (M) are discernible. Magnification×1000.
Figure 10:
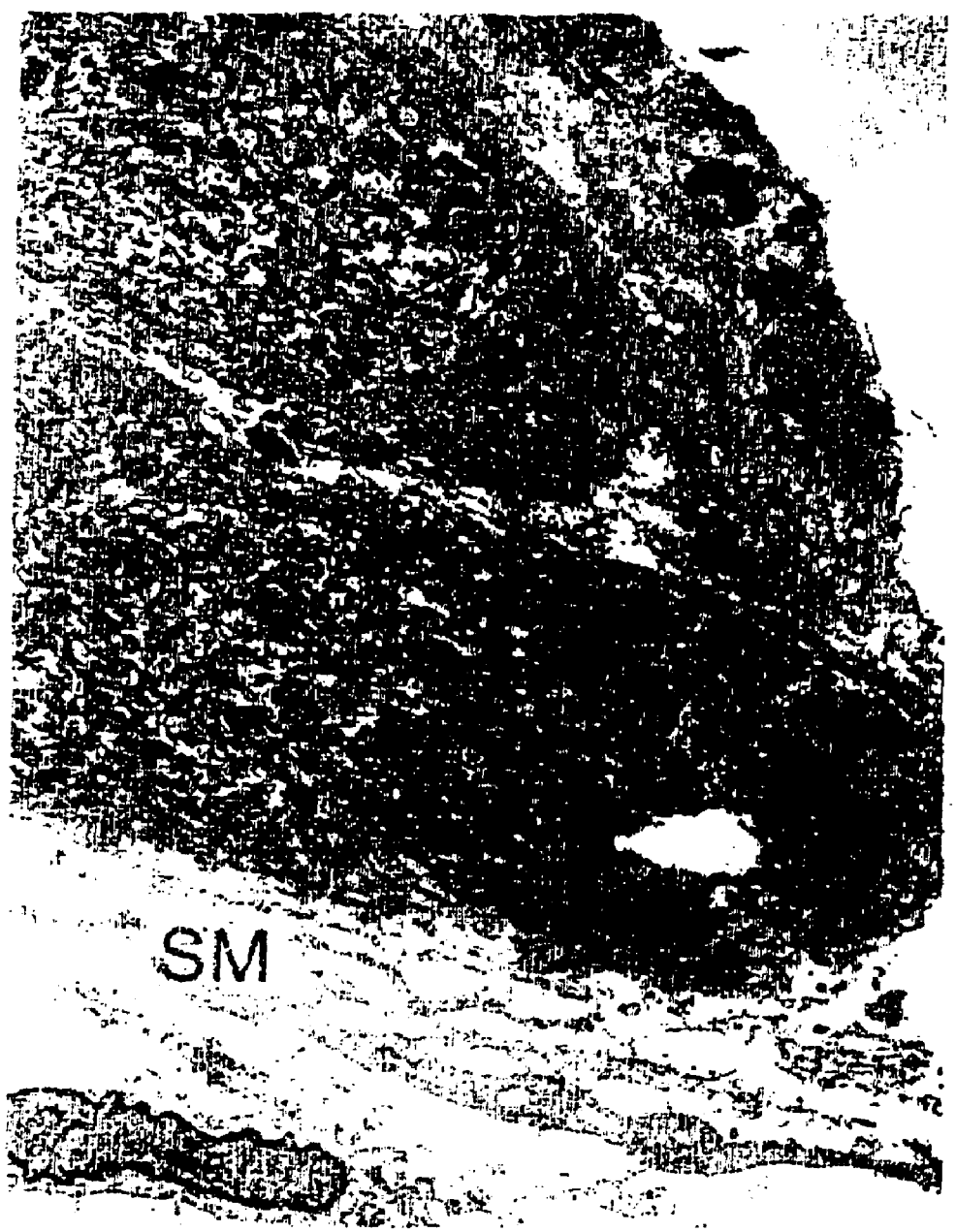
FIG. 10 is a transmission electron micrograph showing thick fibrin plaques in human peritoneal biopsy. This transmission electron micrograph of peritoneal biopsy was obtained upon removal of a catheter during an operation on a patient on peritoneal dialysis, following an episode of peritonitis treated successfully with antibiotics. This shows a thick plaque of recently deposited fibrin (F) exhibiting a network of densely-packed fibrin fibers. The plaque is stratified revealing several serial episodes of fibrin exudation. It lies directly on edematous submesothelial tissue (SM) from which the mesothelial cells have been denuded in the process. Serial biopsies showed that deposits of this depth and fiber density were organized to produce thick, fibrous, scar tissue. Where these fibrin plaques bridged two surfaces, viscera to viscera, viscera to parietum, dense fibrous adhesions were formed. Material collected and analyzed by the International Peritoneal Biopsy Registry. Magnification×7,750.
Figure 11:
FIG. 11 is a scanning electron micrograph of the surface of fibrin plaque in human peritoneal biopsy. A transmission micrograph of the same material is illustrated in the previous figure. This shows a dense, irregular network of fibrin fibers of varying thickness. Magnification×22,500.
Figure 12:
FIG. 12 is a scanning electron micrograph of fibrin clot formed in vitro by the addition of human thrombin (0.5 u) to a solution of human fibrinogen. (Concentration 2 mg/ml) in saline. Magnification×1,620.
Figure 13:
FIG. 13 is a scanning electron micrograph of fibrin clot formed in the presence of synthetic lamellar bodies. This scanning electron micrograph demonstrates fibrin clot formed with identical reactants to that of the control sample illustrated in the previous figure, but has been formed in the presence of synthetic lamellar bodies ($10 \times 10^9$ per ml). The micrograph displays gross differences in the architecture of the fibrin network in comparison to the control. The fibre network is much more irregular and considerably less dense. Compared to the control this sample exhibits large gaps between fibres, accounting for the observed increase in porosity to saline of up to 150% and reduced optical absorbance of light. Magnification 1,620.
Figure 14:
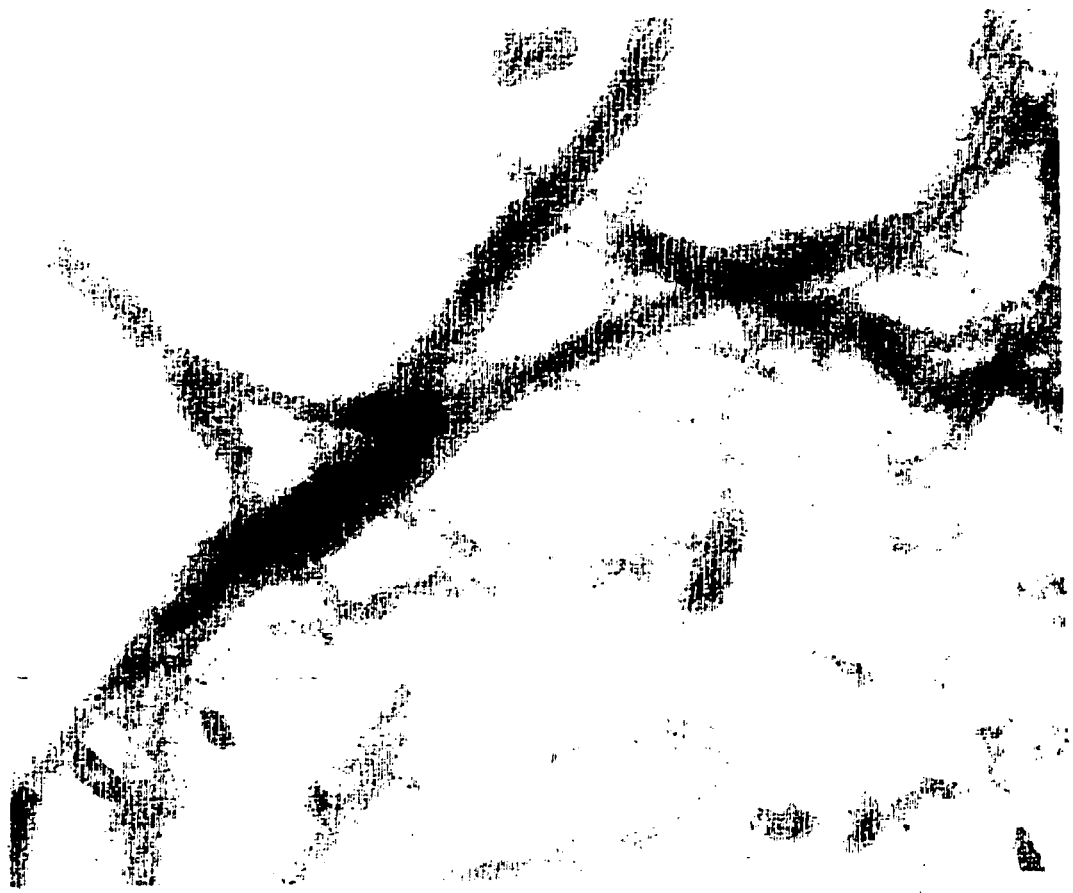
FIG. 14 is a transmission electron micrograph of fibrin clot formed in vitro. This transmission electron micrograph demonstrates a control clot displaying the architecture of the predominantly rectilinear fibrin fibers. Magnification×160,000.
Figure 15:
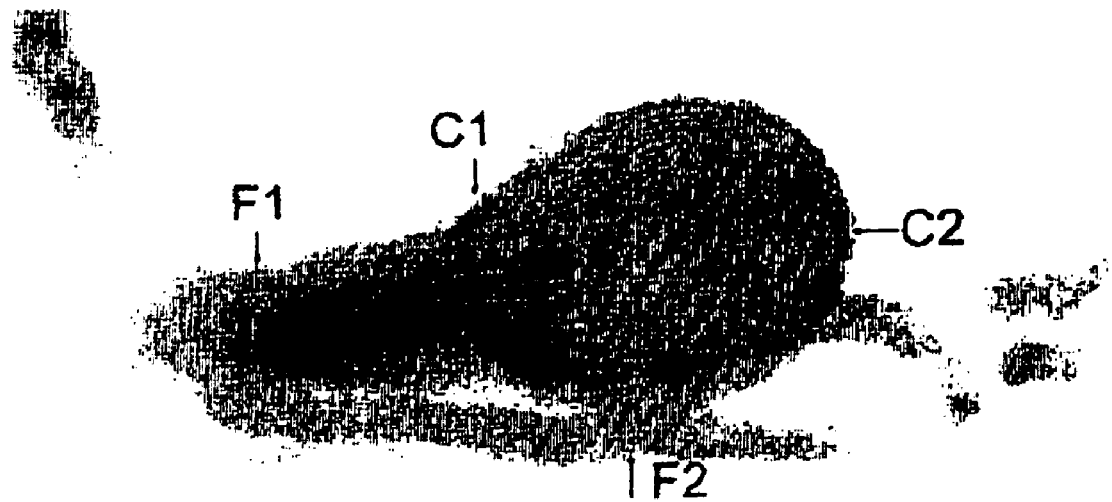
FIG. 15 is a transmission electron micrograph showing synthetic lamellar bodies eroding fibrin fibers. This transmission electron micrograph demonstrates a fibrin clot formed in vitro in the presence of synthetic lamellar bodies at a concentration of $5 \times 10^9$ per ml. The sample taken 2 days after clot formation showed that the fibrin network was evenly permeated by mainly small synthetic lamellar bodies stuck to the fibrin fibres. This micrograph displays the characteristic "snail" like appearance of the synthetic lamellar bodies attached to and merging with the fibrin fibres F1 and F2. The outer surface of the synthetic lamellar body is covered with a fuzzy coat which has the same electron density and texture as the fibrin fibres, and is co-extensive with them at all points of contact (C1, C2). This characteristic appearance of synthetic lamellar body-fibre interaction was widespread throughout the clot network, strongly suggesting that synthetic lamellar body "snails" were actively stripping fibrin branches. These clots were completely dissolved after five days. Mag×195,000.
Figure 16:
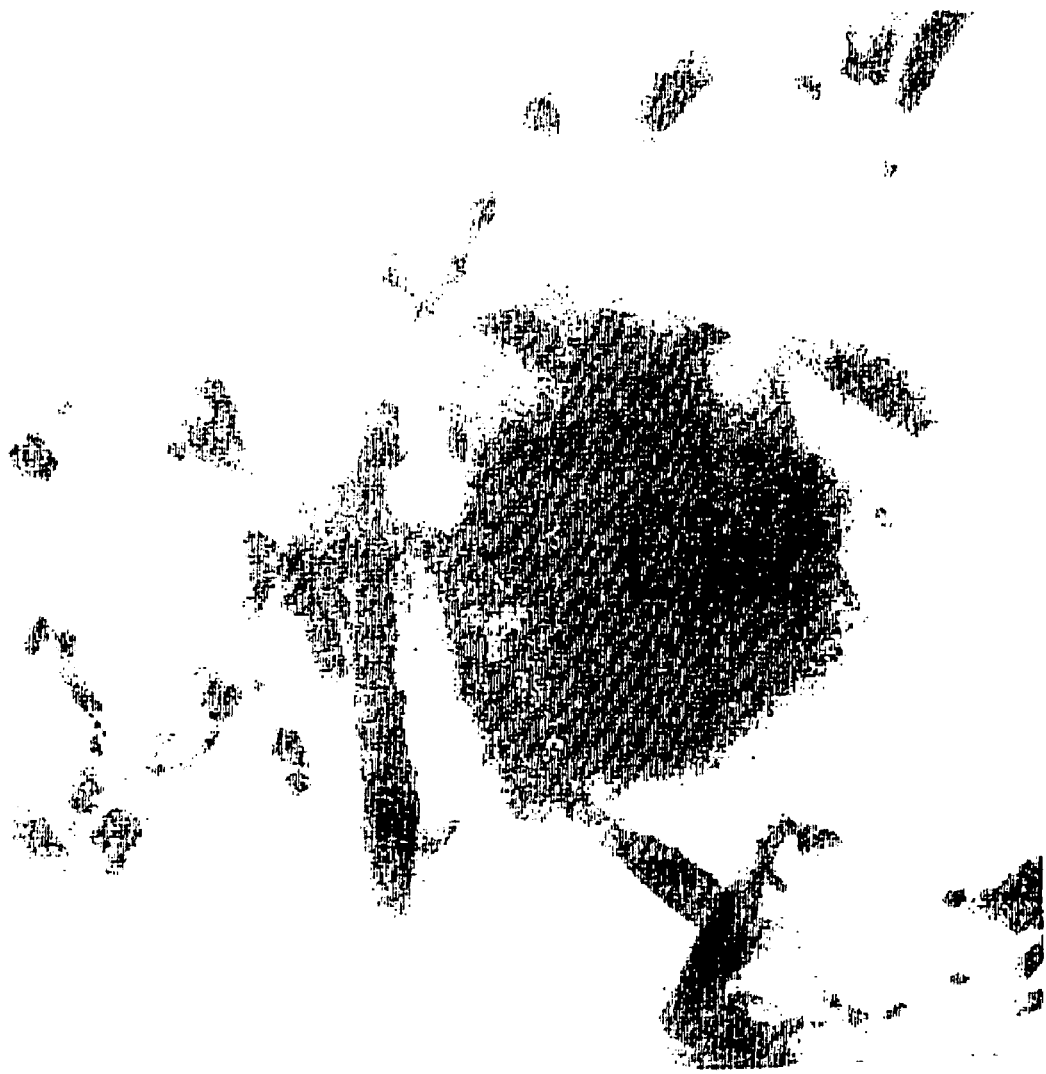
FIG. 16 is a transmission electron micrograph illustrating significant structural disruption of fibrin network by synthetic lamellar bodies. This electron micrograph shows a synthetic lamellar body (L) at the nexus of coverging fibrin fibers. In contrast to the previous two figures, the outer boundary of the synthetic lamellar body is indistinct, being obscured by substantial, irregular, fuzzy deposits which have an electron density and granularity typical of fibrin fibers. These appearances further illustrate the significant structural disruption of the fibrin network caused by synthetic lamellar body presence and activity. Mag×120,000.
Figure 17:
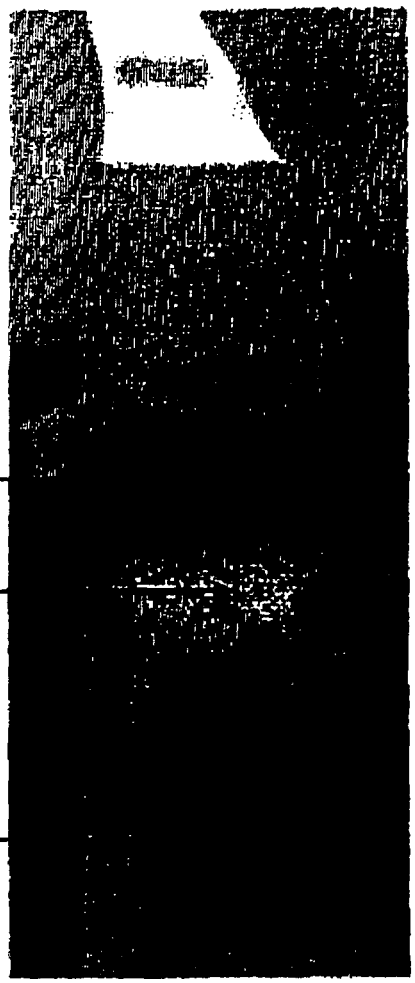
FIG. 17 is an example of fibrin gel dissolution in progress by overlain solution containing synthetic lamellar bodies. This is a photograph of a cuvette containing a pre-formed standard fibrin clot which has been overlain 4 days previously by 1 ml of 0.9% saline solution containing $10 \times 10^9$ synthetic lamellar bodies and incubated at 37° C. At day 4 the underlying fibrin gel is semi-solid, and contains obvious flocculent material. Samples of the gel examined by transmission electron microscopy reveal that the fibrin network is infiltrated with small and larger fused synthetic lamellar bodies. At the interface with the synthetic lamellar bodies solution, there is a thick band of denser flocculent material representing fused synthetic lamellar bodies with adsorbed material derived from the underlying gel. By day 5 the underlying fibrin clot has dissolved, as illustrated in the following figure.
Figure 18:
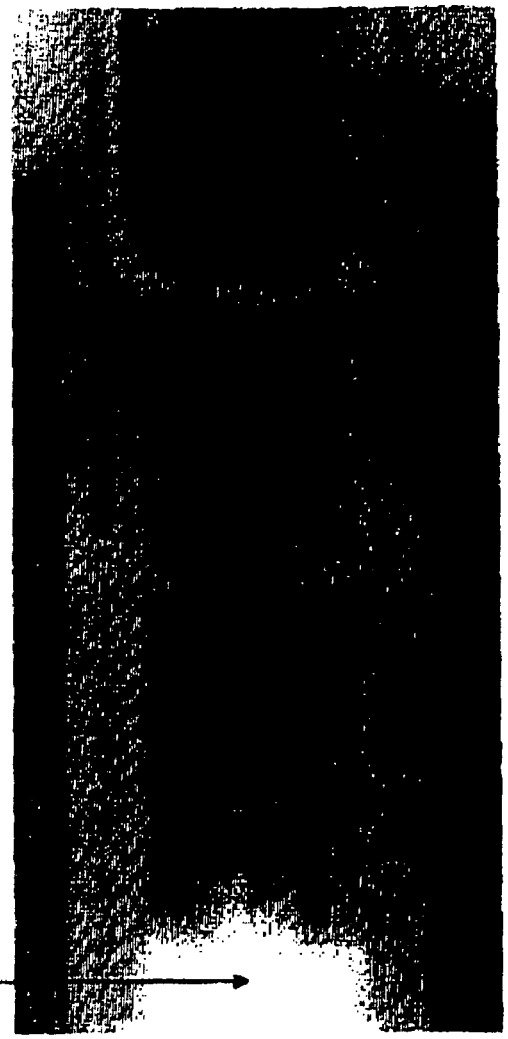
FIG. 18 demonstrates completed dissolution of fibrin gel by synthetic lamellar bodies. This is a photograph of a cuvette, which had contained a pre-formed standard fibrin clot overlain 5 days previously by 1 ml of a 0.9% saline solution containing $10 \times 10^9$ synthetic lamellar bodies and incubated at 37° C. At day 5 the fibrin gel has dissolved and the visible interface containing flocculent material as illustrated in the previous figure which, for the previous 4 days separated the overlying solution containing synthetic lamellar bodies, has sunk to the bottom of the cuvette revealing the dissolution of the fibrin gel. These in vitro experiments demonstrated that, irrespective of whether clots were formed in the presence of synthetic lamellar bodies or the gel was exposed at one interface to a synthetic lamellar body-containing solution, the end-result was clot dissolution in 5 days under similar concentrations and conditions.
Figure 19A:
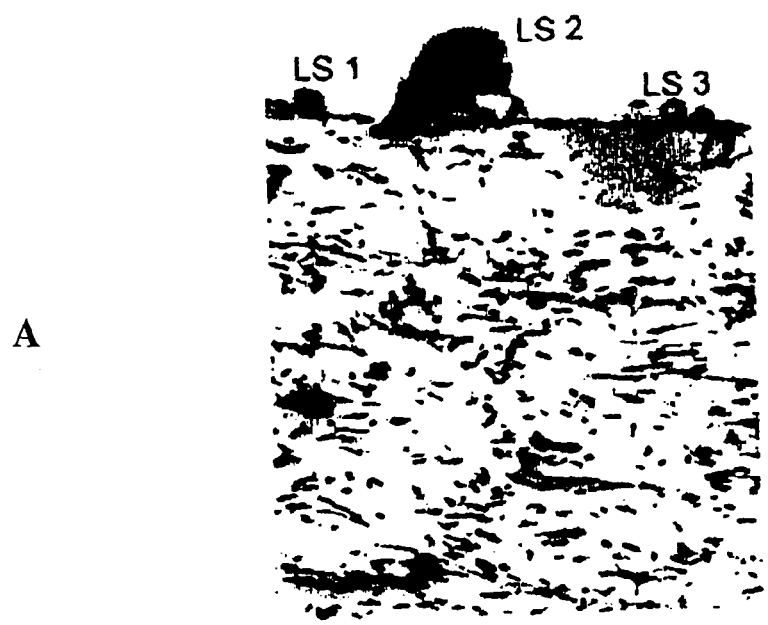
FIGS. 19A and B are transmission electron micrographs demonstrating penetration, then erosion of fibrin clot by overlain solution containing synthetic lamellar bodies. A: is an electron micrograph of fibrin clot whose surface has been sprayed with a solution of synthetic lamellar bodies. This low-power micrograph shows 3 groups of synthetic lamellar bodies, LS1, LS2, LS3 resting on the outer aspect of the fibrin network. The underlying texture of black strands represents fibrin fibres cut in varying cross-section, as they lie within the network of the fibrin gel. Mag×8000. B: shows increased structural detail of the synthetic lamellar bodies on the outer fibers of the fibrin network. Mag×32,000.
Figure 19B:
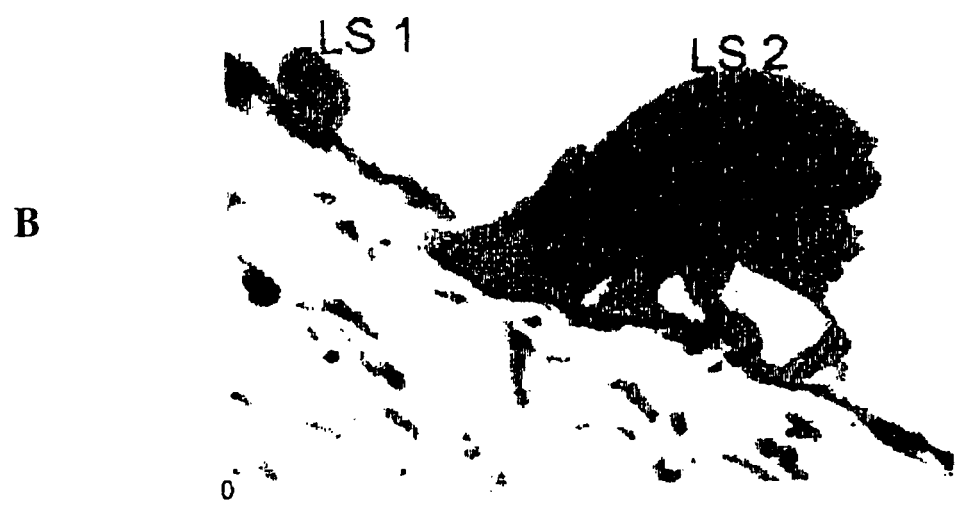
Figure 20:
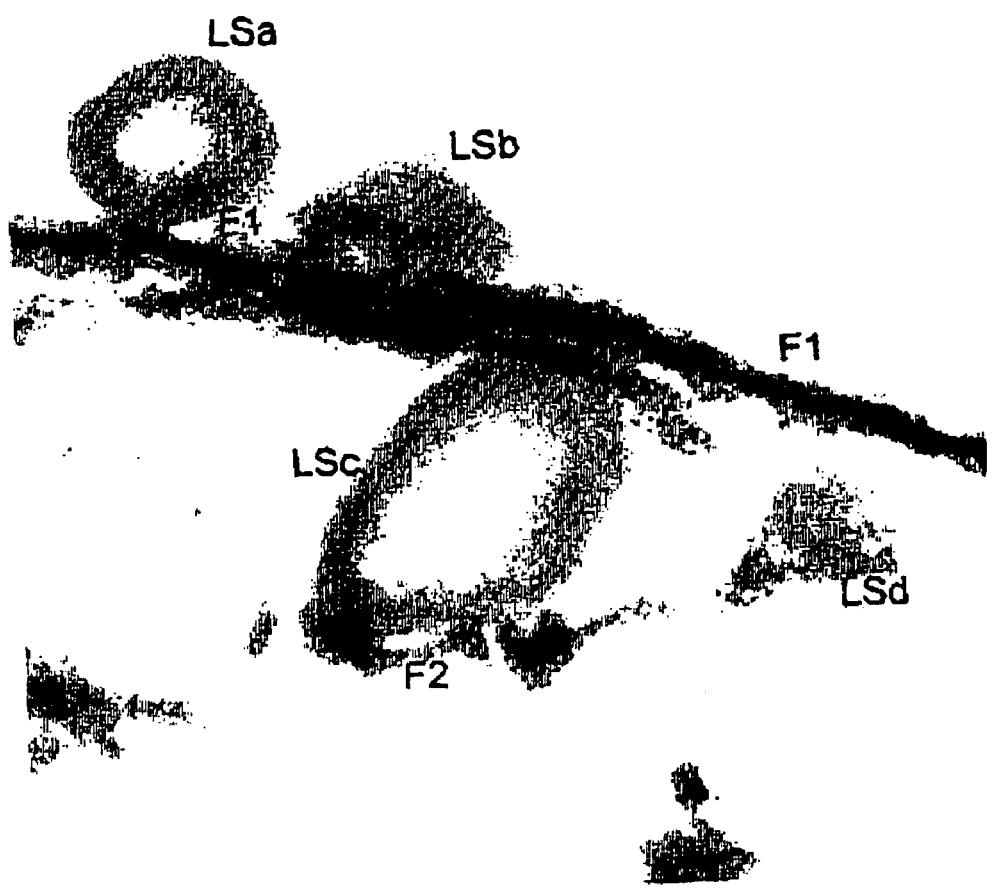
FIG. 20 Transmission electron micrographs demonstrating penetration, then erosion of fibrin clot by overlain solution containing synthetic lamellar bodies. This figure, which is a high-powered detail of an LS3, mag×60,000, shows interaction of synthetic lamellar bodies with fibrin fibers. LSa is attached to fibrin fiber (F1). Synthetic lamellar bodies LSb and LSc are eroding into opposite surfaces of fibrin fiber (F1). LSc on its inner aspect has merged with and is deforming irregular fibrin fiber (F2), which merges with LSd, the fourth synthetic lamellar body in this cluster.
Figure 21:
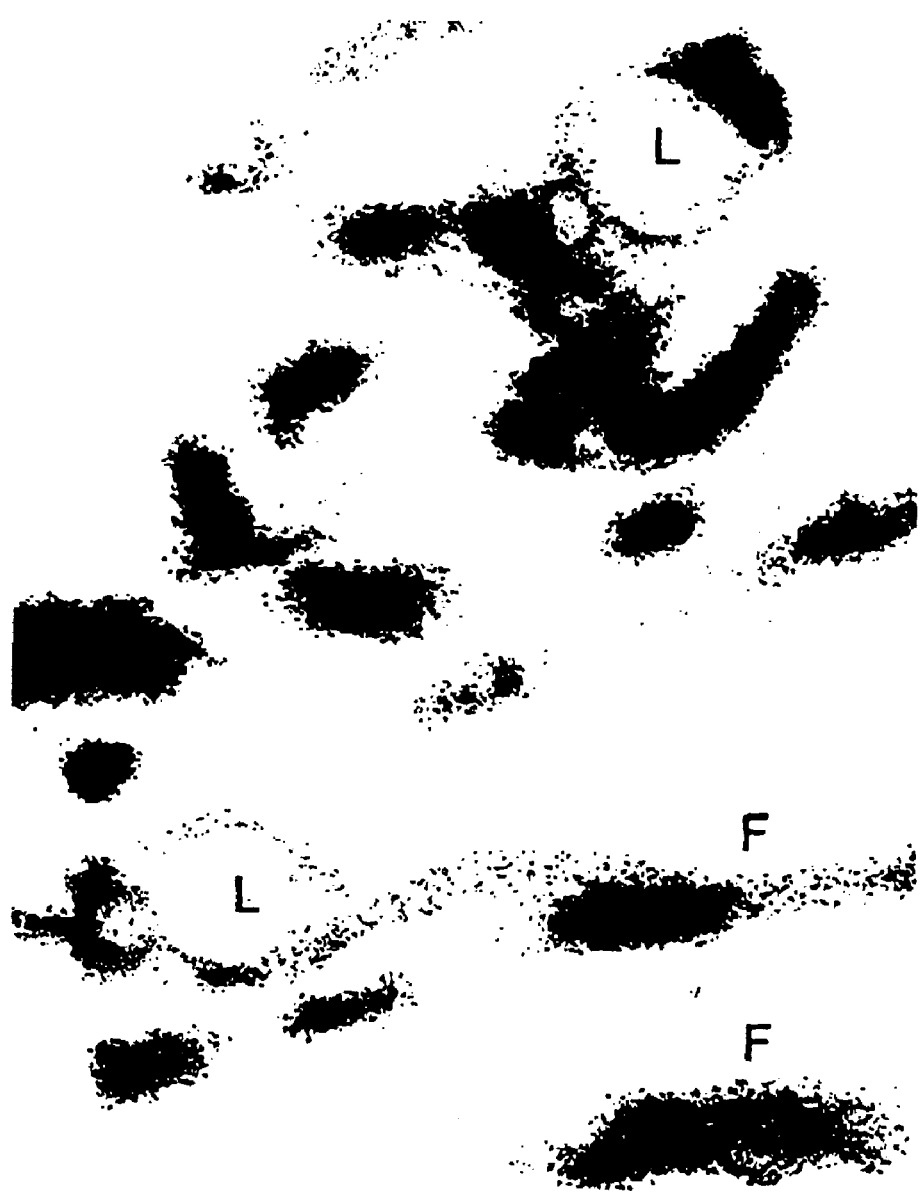
FIG. 21 Transmission electron micrographs demonstrating penetration, then erosion of fibrin clot by overlain solution containing synthetic lamellar bodies. This figure shows the interior of fibrin gel whose surface has, two days previously, been sprayed by lamellasomes®. This shows that the clot has been penetrated by small synthetic lamellar bodies (L), which are evenly dispersed throughout the fibrin network. Small synthetic lamellar bodies are always seen merged with or eroding into fibrin fibers (F). They also show uptake of the electron dense dark granules, which overlay all fibrin fibers. This is suggestive that they are adsorbing and possibly sequestering molecular components of the disintegrating fibers. Mag×120,000.
Figure 22:
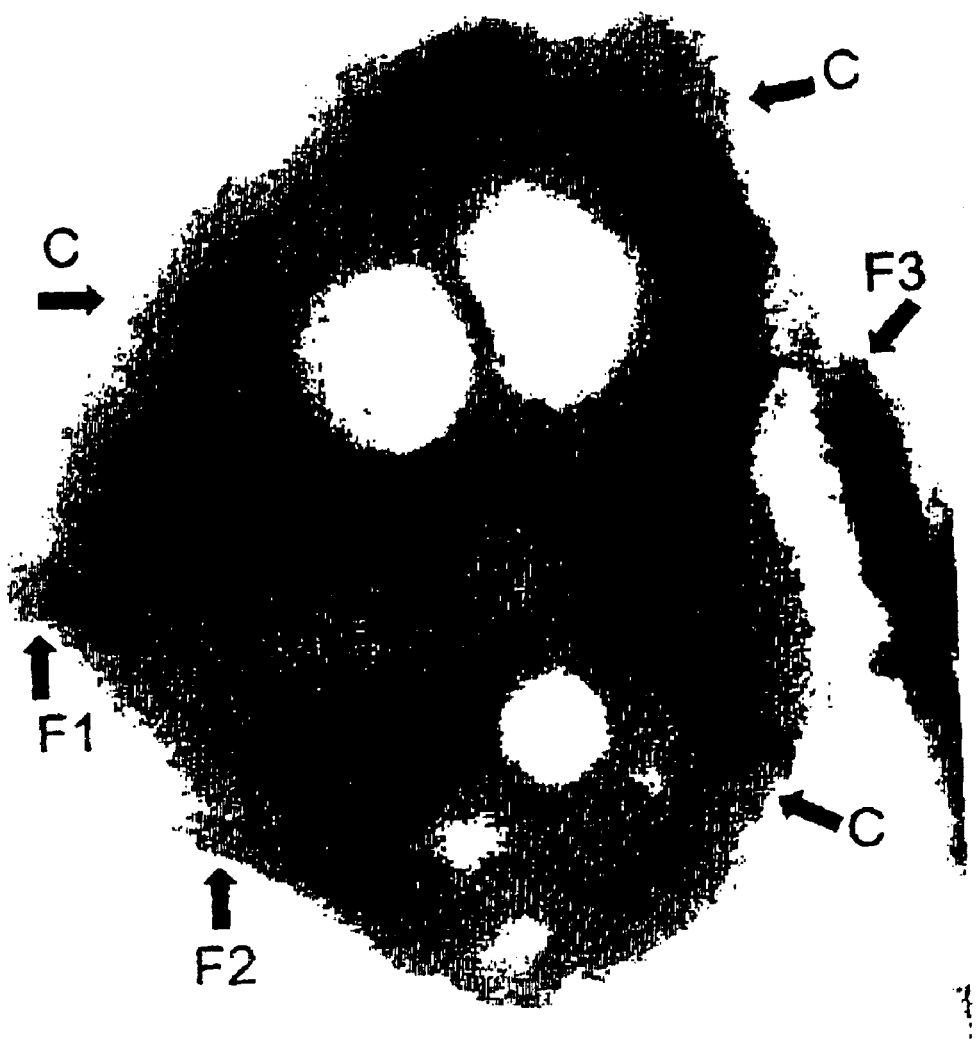
FIG. 22 is a transmission electron micrograph of conglomerate lamellar bodies coated with fragmented fibrin debris. This figure shows large, conglomerate lamellasome® associated with elements of three fibrin fibers (F1, F2, F3). The surface of the synthetic lamellar body is heavily coated with granular material, which has the characteristics of fibrin fiber-derived debris (C). Mag×93,750.
Figure 23:
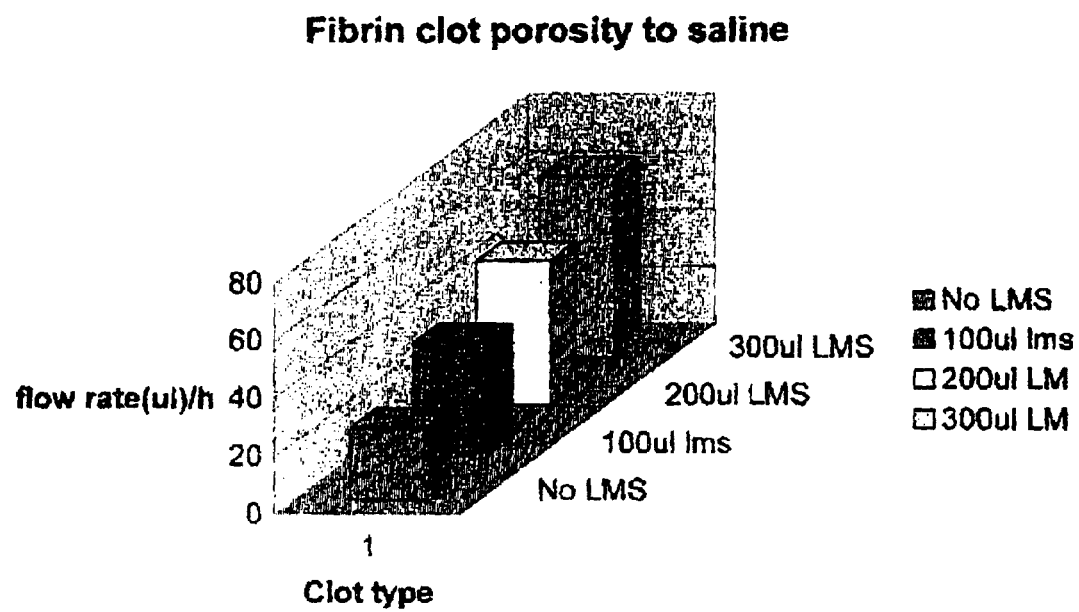
FIG. 23 is a graph illustrating changes in porosity due to incorporation of synthetic lamellar bodies in fibrin clots. This graph illustrates the rate of flow of 0.9% saline through preformed standard 1 ml fibrin clot and 3 clots formed in the presence of different concentrations of lamellasomes®. The clots were allowed to gel in 2 ml syringes for 1 hr at 37° C. Thereafter they were overlain with 2 ml of saline and the flow of fluid through the clot was collected and measured over a 1 hr time period. At the lowest level of lamellasomes® incorporated, the flow-rate of saline increased by 52% compared with control, this rising to 150% increase with the highest level tested (300µ) lamellasomes® conc. $10 \times 10^9$). Experiments of this nature demonstrate the increase in porosity caused by incorporation of lamellasomes® in forming clots.

In a normal peritoneum, the mesothelial surfaces are separated by a thin film of fluid (4µ to 5µ) containing lamellar bodies. The role of this layer is for the reduction of friction and promotion of movement between opposing surfaces, as can be seen in FIGS. 4 and 5. In a response to acute inflammation, this lubricating system is directly opposed by the formation of fibrin, whose prime purpose is the promotion of adhesion and reduction of movement at the locus. Therefore, it inevitably follows that these two systems are in a state of biological balance as, following resolution of an acute inflammatory response, the fibrin is totally removed and the lubricating layer returns, along with movement and function.

In a situation where frequent access to the peritoneal cavity through insertion or removal of catheters, and the four times daily infusion and drainage of 8 to 10 liters of dialysate fluid in hundreds of thousands of patients, the peritoneal cavity acted as a living test tube where its reaction to a wide variety of stimuli was obvious to both patient and medical advisor. It became clear clinically and pathologically that fibrin exudation was a frequent feature of the therapy.

Relatively simple in vitro models have been devised for studying fibrin gelation. Since polymerization of soluble fibrinogen to polymeric fibrin is the central event in intravascular clot formation, the establishment of a model free from the clutter of other blood elements, such as erythrocytes, leucocytes and platelets is important for studying the process in an environment in which the number of variables is limited. Using such a model, the effect of addition or subtraction of individual reactants can be studied with greater confidence in the reliability of findings.

In Vitro Models of Fibrin Gel Networks and Factors Influencing Their Formation

The fibrinogen molecule is an asymmetric rod-shaped dimer (approximately 10×45 nm). On activation, the fibrinogen molecules polymerize by end to end and side to side association, thereby forming protofibrils. The protofibrils associate to form fibrin fibers and the latter join into bundles of larger widths. Protofibrils are believed to be twisted in a helical manner, reflecting an indigenous screw symmetry in the fibrinogen molecule itself. Fibrin fibers are also twisted and grow to a limiting size. The limitation in growth is explained as a consequence of stretching of protofibrils near the surface of the fiber. When the amount of energy necessary to stretch a protofibril exceeds energy available for bonding, lateral growth then ceases.

Hydrated fibrin gels have been studied by a variety of physico-chemical methods, by light and electron microscopy, liquid permeation and turbidity. The gels from normal human fibrinogen were found to be composed of straight rod-like fiber elements, some of which originate from denser nodes. Increasing concentrations of thrombin or fibrinogen form gel networks which become tighter, the fiber strands shorter and the porosity decreases. Gel porosity of the network also decreases in gels formed at increasing ionic strengths. Albumin and dextran, when present in the gel-forming system, are known to produce more porous structures. Thus, albumin is believed to be among the determinants for formation of this type of gel structure in plasma.

Therapeutic Uses of Natural and Synthetic Lamellasome Solutions

The invention provides compositions and methods of treatment comprising administering to a subject an effective amount of the lamellar bodies of the invention. In a preferred aspect, the lamellar bodies or compositions comprising lamellar bodies are substantially purified (e.g., substantially free from substances that limit its effect or produce undesired side-effects). The subject is preferably an animal, including but not limited to animals such as monkeys, cows, pigs, horses, chickens, cats, dogs, etc., and is preferably a mammal, and most preferably human. In one specific embodiment, a non-human mammal is the subject. In another specific embodiment, a human mammal is the subject. As synthetic lamellar bodies mimic the action of natural lamellar bodies, both of these can be used as therapeutic agents for a number of uses. Synthetic lamellar body solution, with and without addition of hyaluronan and/or chondroitin sulphate B, provides a method of modifying the deposition and/or removal of fibrin in situ in most tissues, cavities, blood vessels and ducts without requiring anticoagulants or proteolytic fibrinolytic enzymes which have life threatening systemic side effects. Thus, the key role of synthetic or natural lamellar bodies in therapies is the provision of targeted local modification or lysis of fibrin or whole blood clots. This means that synthetic lamellar bodies can be used in therapies where anti-adhesion or anticoagulant properties are required.

In particular, lamellar bodies can be used in the treatment of two principle groups of disorders:

a) The restoration of normal structures and function in sites subjected to acute inflammatory reaction, through the removal of extravascular fibrin to permit healing by first intention. Lamellar bodies can be used to prevent or modify the formation of granulation tissue, thus preventing scarification and loss of function.

b) Lamellar bodies can also be used to treat intravascular and extravascular whole blood clot formation. Synthetic lamellar bodies will be used to either prevent or modify intravascular clotting in confined segments of the vascular tree. This can be used as a preventative measure in situations involving vascular surgery and intra-vessel manipulations, such a coronary angioplasty, resulting in procoagulant activity and/or micro-emboli in distal arteriolar and capillary beds. Synthetic lamellar bodies can be used to treat intravascular thrombosis by being injected into preformed clots in vessels of all calibers in the arterial tree. Synthetic lamellar bodies in solution may also be used to liquefy hematomas by direct injections. This treatment would be applicable where local swelling is causing acute functional compromise or where more rapid dispersal of hematoma by synthetic lamellar bodies would prevent slow healing by granulation tissue, causing scarification and disfigurement.

Furthermore, many treatments of the vascular system entail the introduction of a device such as a stent, catheter, balloon, guide wire, cannula or the like. One of the potential drawbacks to the use and implantation of these devices is that blood vessel walls can be disturbed or injured. Clot formation or thrombosis often results at the injured site, causing stenosis (closure) of the blood vessel.

Another cause of stenosis is vascular disease. Probably the most common disease causing stenosis of blood vessels is atherosclerosis. Atherosclerosis is a condition which commonly affects the coronary arteries, the aorta, the iliofemoral arteries and the carotid arteries.

Many medical devices and therapeutic methods are known for the treatment of atherosclerotic disease. One particular therapy for certain atherosclerotic lesions is percutaneous transluminal coronary angioplasty (PTCA). Another therapy for certain atherosclerotic lesions is percutaneous transluminal angioplasty (PTA). During PTA, a deflated balloon-tipped catheter is inserted in a patient's artery. The tip of the catheter is advanced to the site of atherosclerotic plaque. Inflation of the balloon "cracks" the atherosclerotic plaque and expands the vessel, thereby relieving the stenosis, at least in part.

While PTA presently enjoys wide use, it suffers from two major problems. First, the blood vessel may suffer acute occlusion immediately after or within the initial hour after the dilation procedure. Such occlusion is referred to as "abrupt closure." A second major problem encountered in PTA is the re-narrowing of an artery after an initially successful angioplasty. This re-narrowing is referred to as "restenosis" and typically occurs within the first six months after angioplasty. Restenosis is believed to arise through the proliferation and migration of cellular components from the arterial wall, as well as through geometric changes in the arterial wall referred to as "remodeling."

A device such as an intravascular stent including stent grafts and covered stents can be a useful adjunct to PTA, particularly in the case of either acute or threatened closure after angioplasty. The stent is placed in the dilated segment of the artery to mechanically prevent abrupt closure and restenosis. Unfortunately, even when the implantation of the stent is accompanied by aggressive and precise antiplatelet and anticoagulation therapy (typically by systemic administration), the incident of thrombotic vessel closure or other thrombotic complication remains significant, and the prevention of restenosis is not as successful as desired. Furthermore, an undesirable side effect of the systemic antiplatelet and anticoagulation therapy is an increased incidence of bleeding complications, most often at the percutaneous entry site.

Thus, the use of the lamellar bodies of the present invention may prove beneficial in treatment of patients undergoing angioplasty or stent implantation to prevent the potentially life threatening thrombotic complications of such therapies.

Surgical Use of Lamellar Bodies

Synthetic lamellar bodies can also be used as anti-adhesion agents in all forms of surgery. In particular, lamellar bodies in solution can be used in operative procedures in peritoneal, pleural, pericardial, joint cavities and tendon sheaths. Lamellar bodies may be used in gynecological surgery. Lamellar bodies may also be used in neurosurgery. Lamellar bodies may also be used in eye or ear surgery.

The Use of Lamellar Bodies in Gynecological Operations

Gynecological conditions including, but not limited to, uterine fibroids, endometrial hyperplasia, endometriosis, and ovarian cysts are common in many women. The primary means of alleviating the pain or discomfort associated with these conditions is through surgery.

For example, more than 30% of women develop fibroids by the time they reach menopause. Fibroids are benign adenomas composed of fibrous tissue which originate in the uterine wall. In some situations, the fibroids may be small and the individual may not exhibit any symptoms at all. On the other hand, certain women experience severe menstrual bleeding and cramping, or constipation and urinary frequency due to the large size of the fibroids. As noted above, the usual treatment for fibroids is surgical removal (ie. hysterectomy or hysterotomy).

Endometrial hyperplasia, which is an abnormal thickening of the endometrium that is not completely shed at the time of menstruation, is thought to affect between 5-15% of pre-menopausal women. The symptoms, which can include painful and heavy menstruation, and painful sexual intercourse, can be alleviated usually through surgical intervention (ie. curettage or hysterectomy).

Endometriosis, which affects about 5% of pre-menopausal women, is due to the appearance of patches of endometrial tissue in the peritoneal cavity. Generally, these patches of endometrium, which can grow on the serosal surface of the ovaries, uterus, bladder, large intestine or the peritoneum, respond to normal hormonal changes over the menstrual cycle in parallel to that of the endometrium. Thus, the areas containing this endometrial tissue can bleed, swell and cause severe pelvic discomfort and pain. As with other gynecological problems as noted above, the standard therapy for endometriosis is surgical ablation of the abnormal tissue. However, the recurrence rate is high, requiring ongoing surgical treatment (Namnoum et al. (1995), "Incidence of symptom recurrence after hysterectomy for endometriosis." Fertility and Sterility, 64(5): 898-902).

Ovarian cysts are thought to affect an even higher percentage of pre-menopausal women, in fact, up to about 20%. The pathology is that of multiple, incomplete follicles within the body of the ovary. Polycystic ovarian disease, which is characterized by excessive androgen production from the follicles stimulated by abnormally high insulin levels, is a variant of this condition. The usual symptoms of polycystic ovarian disease are hirsutism and acne. While the normal treatment for these conditions is the use of agents that down-regulate the release of gonadotrophins (FSH and LH) from the hypothalamus (thereby inhibiting ovulation), surgical intervention may be necessary in extreme cases.

The surgical procedures necessary to treat the above noted conditions may be beneficial in alleviating the pain and discomfort associated with these conditions, but there is always a risk for formation of post-surgical adhesions. Accordingly, the methods and compositions of the present invention, as described below, may be beneficial when used in conjunction with the surgical procedures noted above.

The Use of Lamellar Bodies in Operations in the Peritoneal Cavity

In open abdominal surgery, the surfaces of visceral and parietal peritoneum, in as wide an area as possible, are lightly sprayed with 2 ml of synthetic lamellar bodies before any surgical manipulation is carried out. The synthetic lamellar bodies with their entrapped fluid become enmeshed in the dense microvillous surface carpet of the exposed mesothelial cells, before the deleterious effect of air drying commences. A thin layer of synthetic lamellar bodies protects the mesothelium from drying. The synthetic lamellar bodies are therefore in situ in increased density at the beginning of the operation, where the abnormal stimulus of opening the cavity induces fibrinogen exudation and fibrin deposition over the surface of the exposed peritoneal lining. Thus the fine fibrin network which typically develops at the beginning of operative procedures will take place in an environment of increased density of synthetic lamellar bodies. Extravascular fibrin clots formed ab initio will therefore contain synthetic lamellar bodies, resulting in the formation of a fibrin network which is less dense than normal and which will be open to fibrinolytic degradation by synthetic lamellar bodies and the fibrinolytic system.

The median dose that is sprayed on each occasion when used is 1 ml. In a preferred embodiment, the ideal concentration of synthetic lamellar bodies is $10 \times 10^9$/ml. 100 microliters of synthetic lamellasome solution sprayed evenly will cover 1 $m^2$ of peritoneal surface to a depth of 3µ. According to the nature of the operative procedure, a further 1 ml of synthetic lamellar body solution should be sprayed over the entire operative area every 30 minutes throughout the procedure. A final 2 ml of synthetic lamellar body solution should be sprayed evenly around the peritoneum immediately before closing the abdomen. In an abdominal operation lasting 4 hours, the total volume of synthetic lamellar body solution applied is about 10 ml.

In a preferred embodiment, the standard method for preparing abdominal surgery would include the steps:

making an incision in the abdominal cavity in order to expose a surgical site;

removing or modifying tissue at the original site; and reclosing the abdominal cavity.

Alternatively, another preferred embodiment would be:

making an incision in the abdominal cavity in order to expose a surgical site;

removing or modifying tissue at the surgical site;

applying a composition, including lamellar bodies, to at least part of the surgical site; and reclosing the abdominal cavity.

This use of lamellar body solutions can be both for the treatment of surgical adhesions and to prevent the formation of said surgical adhesions.

Synthetic lamellar body solutions should be used in laparotomies carried out for adhesiolysis in a similar manner to that described for open abdominal surgery. Again in laparascopic abdominal surgery using the technique of pneumoperitoneum, the peritoneum must be sprayed with a median dose of 1 ml at the beginning of the operation and at a median of every 30 minutes throughout the procedure.

Synthetic lamellar bodies that are sprayed into the peritoneal cavity are removed post-operatively by drainage through the opercula of the lymphatics in both domes of the diaphragm, passing through the thoracic duct into general circulation. Synthetic lamellar bodies are readily phagocytosed (as are natural lamellar bodies) by the reticulo-endothelial system. The load obtained through use of a total median dose of 10 ml in a four hour operation would cause no overloading of the reticulo-endothelial system. In addition to this route of dispersal of synthetic lamellar bodies, there are two other principle modes of uptake in metabolism. As with natural lamellar bodies, synthetic lamellar bodies are phagocytosed by peritoneal macrophages which recycle the phospholipids, as occurs in pulmonary alveoli, for absorption by mesothelium as a substrate to produce new lamellar bodies. Thus, any excess of synthetic lamellar bodies in the post operative period provide a large pool of phospholipid substrate to support high levels of lamellar body production. The maintenance of lamellar body secretion in the early post-operative period serves not only the down regulation of extravascular fibrin formation, but enhances the non-stick role in reducing friction between the layers of the peritoneum.

Characteristically, the junctional regions between mesothelial cells is sloping. Thus mesothelial cells overlap. Mesothelial cell nuclei show specific nuclear characteristics found in cells subjected to extremes of stretching. Thus, mesothelium in areas which can expand up to 10 times their normal circumference must be subjected to large increases in surface area in order to maintain an intact cellular cover. Lamellar bodies secreted onto the lumenal surface by mesothelium pass between the cells into the junctional regions, where they are located in normal peritoneum. Their regular presence in the sloping, elongated junctional regions serves as an important function in allow frictionless sliding between cell borders to allow stretching without exposing bare areas between cells. Providing an excess of synthetic lamellar bodies in the postoperative period, where the inflamed submesothelial tissue shows varying degrees of oedema and stretching of the overlying mesothelium, serves as an important added protection against the splitting and separation of mesothelial cell layer and continuing the post-operative oozing of fibrinogen and fibrin formation.

Operations in Other Serous Cavities

Procedures using lamellar bodies in solution are applicable in the prevention of adhesions during surgery carried out in the pericardial and pleural cavities. In the past, there was a disregard of the occurrence of pericardial adhesions to the chest wall, as interference with cardiac movements were not considered detrimental to cardiac function. Also, it was believed that a single open cardiac operation was all that an individual patient would require in his remaining lifespan. However, more recently serial cardiac operations have become increasingly common. This means that the time spent by the surgeon in laborious dissection of adhesions between the heart and anterior chest wall has added considerably to both time and difficulty in clearing the area prior to an operation being carried out. The administration of lamellar body solution on opening the pericardial cavity can be carried out as in abdominal operations, with an initial spraying of 1 ml to parietal and visceral pericardium.

Lamellar body solutions may also be used in lung surgery to maintain a freely mobile pleura. In several disorders and surgical situations, pleural adhesion may be beneficial and lamellar body solutions would therefore not be used. However, a mobile pleura free of adhesions may be important where there are pleural tumor seedlings and access to all of the cavity for intra-pleural chemotherapy must be maintained. In particular, dense fibrin containing tumor seedlings produce densely collagenous adhesions sequestering metastatic deposits inaccessible to anti-tumor agents. Furthermore, clinical observations as well as experimental models of tumor cell adhesion have shown that damaged tissue is an attractive site for tumor growth after systemic injection of viable tumor cells. See, for example, S. Murthy and E. Scanlon, eds., Injury and Tumor Implantation: Biological Mechanisms and Clinical Implications for Recurrence and Metastasis. R.G. Landes Co., Austin, Tex. 1993. The results show that specific adhesion molecules and their receptors play a role in tumor cell and endothelial cells or extracellular matrix attachment. B. Zetter, Seminars in Cancer Biology, 4: 219-229 (1993). There are numerous adhesion molecules which are expressed by tumor cells and which are stimulated by various environmental conditions or factors, e.g., cytokines. Accordingly, it may be beneficial to utilize the lamellar bodies or compositions comprising lamellar bodies to prevent the possible attachment of metastatic tumor cells to exposed (damaged) tissue following surgery.

Incorporation of Other Therapeutic Agents in Lamellar Body Solutions

The present invention also encompasses the option of incorporating other active agents on and within the lamellar bodies to effect and provide targeted therapeutic benefit during surgery. For example, in peritoneal endometriosis, lamellar bodies can be prepared to contain anti-estrogen compounds which will serve to suppress endometrial epithelium, as well as suppressing focal dense fibrin formation following adhesiolysis (lysis of adhesions). Examples of such anti-estrogen compounds may include those known as aromatase inhibitors, including aminoglutethimide (Cytadren) or anastrozole (Arimidex). Other anti-estrogen compounds may be selected from the class of compounds known as estrogen receptor blockers, including clomiphene (Clomid) and tamoxifen (Nolvadex), which are the most popular drugs of this class. They are more precisely referred to as "selective estrogen receptor modulators." This is because their mode of action is not so simple as merely blocking the estrogen receptor. Estrogen receptors require not only hormone but also activation of regions of the receptor called AF-1 and AF-2. AF-1, to be activated, requires phosphorylation, while AF-2 can be activated by any of a number of cofactors, such as IGF-1. As it happens, clomiphene and tamoxifen are estrogen receptor antagonists (blockers) in cells that depend on activation of the AF-2 region, while in cells which activate AF-1, these compounds are estrogens. In some cells these drugs activate one of the types of estrogen receptor (ERa) but are antagonists of the other type (ERb). The result is that these compounds are antiestrogenic in breast tissue, fat tissue, and in the hypothalamus, but are estrogenic in bone tissue and with respect to favorable effect on blood lipid profile, both of which are, again, desirable. They also appear to have some estrogenic effect on mood, though this may be in only parts of the brain. Cyclofenil is a similar drug to the above two. Raloxifene (Evista) is a new selective estrogen receptor modulator that, for women, has the advantage of being an antiestrogen in the uterus, whereas clomiphene and tamoxifen are estrogens in that tissue. For this reason, the latter two drugs can promote uterine cancer, while raloxifene actually should help prevent it, and is therefore a superior drug for women.

Also, lamellar bodies containing chemotherapeutic antitumor agents can be used during operations in patients with abdominal carcinomatosis, as peritoneal tumor deposits classically seed onto denuded areas of the peritoneum, becoming enmeshed in fibrin clots and forming dense adhesions containing sanctuary areas of metastatic tumor deposits. Examples of antitumor agents include bleomycin hydrochloride, methotrexate, actinomycin D, mitomycin C, vinblastine sulfate, vincristine sulfate, daunorubicin hydrochloride, adriamycin, neocarzinoszatin, cytosine arabinoside, fluorouracil, tetrahydrofuryl-5-fluorouracil krestin, picibanil, lentinan, levamisole, bestatin, azimexon, glycyrrhizin, poly I:C, poly A:U, poly ICLC, cisplatin and the like. This therapeutic strategy is also applicable to pleural and pericardial cavities.

Lamellar Body Solutions Used in Surgery of Synovial Joints and Tendon Sheaths

Lamellar body solutions can be used in open and arthroscopic surgery to modify fibrin deposition and to promote healing by first intention by suppressing scarification and preventing joint adhesions. Appropriately, reduced volumes of lamellar body solution, depending on the size of the joint space, should be used.

Other agents that may be envisioned for combination therapy for use with the lamellar bodies may be anti-inflammatory agents, or analgesic agents suitable for treatment of pain. Examples of analgesic agents include salicylic acid, acetaminophen, ibuprofen, flurbiprofen, morphine and the like; local anesthetics such as lidocaine, bupivacaine, benzocaine and the like. Examples of anti-inflammatory agents may be hydrocortisone, prednisone and the like. Furthermore, antibacterial agents such as penicillin, cephalosporins, bacitracin and the like may be used in combination with the lamellar bodies of the present invention.

Lamellar body solutions can be used in operations on tendons to spray visceral surfaces when exposed, as well as spraying the outer aspects of the tendon sheath to prevent the formation of dense fibrin clots.

Use of Lamellar Body Solutions in Neurosurgery

In peripheral nerve surgery, lamellar body solutions and sprays should be used when surgery is carried out on the perineureum.

In intra-cranial and intra-spinal surgery, the meninges are also subject to acute inflammatory reaction to surgical interference, as in other body cavities. Where fibrin exudation may result in scarification with dysfunctional effects, the use of lamellar body solution is an option. Likewise, cerebrospinal fluid also contains lamellar bodies secreted by the ependyma. Therefore, operations to relieve intra-cisternal blockage may benefit from the use of lamellar body solutions to counteract any procoagulant activities stimulated by surgery, which would otherwise reverse the intended outcome of the surgical procedure.

In rheumatoid arthritis, acute inflammation is the cyclic pathological process, which leads to joint destruction. In acute inflammation there is a massive exudation of fibrinogen from the hyper-permeable vessels of the highly vascular, inflamed synovium. Thus, fibrin is deposited in peri-articular tissues and the joint of space. In rheumatoid arthritis, fibrin can account for up to 34% of the volume of synovial fluid where it is present as so called rice bodies and flakes, while thick stratified layers cover all of the joint surfaces. Fibrin networks are also widely infiltrated throughout the peri-articular tissues. The repeated widespread deposition of fibrin in the granulation tissue and joint spaces results in healing by second intention, leading to fibrous adhesions, scarification and obliteration of joint space. It is worth noting that intra-articular deposition of fibrin is also a feature of other types of acute joint inflammation, as in gout, pseudo-gout and Reiters Disease.

Intra-articular injections of lamellar body solution can be used in acute joint inflammation to prevent the formation of dense fibrin clots, and to promote fibrin fragmentation and dissolution. This can be carried out in conjunction with administration of anti-inflammatory medication.

Therapeutic Uses of Lamellar Bodies (Synthetic or Natural) in Disorders of the Middle Ear and Eustachian Tube The Eustachian tube connects the cavities of the middle ear with the pharynx. Its sole function is the equalization of air pressure on both sides of the eardrum. If the Eustachian tube is blocked, the air pressure in the middle ear rises, causing increasing diminution of auditory acuity. In 1982 it was discovered that lining cells in the Eustachian tube secreted pulmonary surfactant. To this day it is not widely appreciated by otolaryngologists that this esoteric finding is of crucial importance in the causation of disease in this part of the body. The surfactant property of the lamellar bodies secreted in this duct perhaps has obscured their understanding that the principle role of lamellar body secretion is not that of a surfactant, but of providing non-stick surfaces which are capable of de-blocking fibrin exudates and plugs.

The Eustachian tube guards a vital function in animal survival by protecting the auditory acuity of both predator and prey. In hominids the recent adoption of the upright position has resulted in sub-optimal drainage of the middle ear, since there has been insufficient evolutionary time for modification of a system standard in all quadrupeds of a horizontal skull and constant forward movement. This anatomical deficit, together with the recent crowding together of the species in large groups, has resulted in a situation where otitis media with effusion or "glue ear" is a present-day epidemic affecting up to one third of all children at some time in their early lives (Bull P D. In: Diseases of the ear, nose and throat. Blackwell Science Ltd. Oxford. 1996. pp 57-60). This condition is due to the accumulation of fluid, often viscous, within the middle ear cleft through blockage of the Eustachian tube and resultant poor drainage into the pharynx. This leads to significant conductive deafness causing developmental and educational impairment.

The pathology of this condition derives from acute inflammation of the Eustachian tube through extension from the pharynx of viral and/or bacterial infection. As at all sites, the acute inflammatory exudate contains a high proportion of extravascular fibrin whose function is to localize the infection and prevent its spread. Again, massive or persistent fibrinous exudate will heal by second intention, causing sub-mucosal fibrosis, lumenal synechia (fine adhesions), narrowing and blockage of the duct. As at other sites, the pathological sequelae derive from the overwhelming of the lamellar bodies' ability to ensure early removal of extravascular fibrin. Thus the use of lamellar body solution at an early and appropriate stage, through administration on a continuous or intermittent basis by direct injection or through gromits which give access to the middle ear and Eustachian tube will modify fibrin in formation while also lysing pre-formed old fibrinous exudate.

The problem is particularly noticeable in cases of Chronic Otitis Media (COM). Accordingly, in cases such as this, one suggestion is to treat the problem surgically by introducing a composition comprising lamellar bodies into the middle ear. This is done by inserting a fine needle through the tympanic membrane (which may have an incision made in it) and introducing the composition comprising lamellar bodies through the fine needle into the middle ear. The lamellar bodies are then allowed to modify this viscosity of the fibrin in the middle ear, such that it is capable of draining from the middle ear. The modified fibrin can be drained through the incision in the tympanic membrane and a vent tube can be inserted into the tympanic membrane to close the incision.

Novel Use of Lamellar Bodies in the Treatment of Lung Disorders

Results of Re-appraisal of Fibrin in Lung Pathology

The findings of our in vitro investigations carried out in respect of the present invention of the highly potent biological action of lamellar bodies on the formation and removal of fibrin has occasioned a critical re-appraisal of the validity of established concepts of the aetiopathogenesis of all lung disorders involving an inflammatory response. These findings reveal the existence of a hitherto unrecognized pivotal role of lamellar bodies in the successful resolution of pulmonary diseases, which involve acute inflammation and its inevitable deposition of intra-alveolar fibrin. Obversely, any disorder which reduces pulmonary lamellar body secretion, can now be predicted to have serious pathological effects on the resolution of the inflammatory response by virtue of the failure to promote early removal of fibrin, resulting in healing by second intention, granulation tissue and fibrosis. Thus the role of lamellar bodies as surrogate lamellar bodies assumes novel therapeutic potential for the better resolution of most, if not all, lung disorders where intra-alveolar exudation of fibrin occurs.

Crucial Role of Pulmonary Alveolar Architecture in Nature of Inflammatory Response Pulmonary alveoli possess microscopically-thin walls, 20-40 microns in thickness, which contain the rich capillary network. If an inflammatory-provoking agent succeeds in passing through the proximal respiratory passages, an acute inflammatory reaction will take place in a region with a highly delicate microscopic architecture which subtends the air sacs. Thus, by virtue of the hyper-vascularity of the thin-walled, honeycombed structure of the lung, it is obvious that the effect of the effusion of fibrin in such a site would have immediate and catastrophic effects on pulmonary function. As in other sites, acute inflammation results in vascular congestion of the capillary network in the alveolar walls, leading to margination of granulocytes, increased permeability of the vessel walls and effusion of fibrinogen-rich exudate around and through the pulmonary epithelium into the alveolar space. Fibrin is thus deposited around the walls of the air sacs in a situation where Type II pneumocytes secrete lamellar bodies as pulmonary surfactant.

Because of the absence of any knowledge in the biological or medical world of the effect of lamellar bodies, as demonstrated by our research with synthetic lamellar bodies on fibrin formation and removal, from this point on, any current explanation of the course of pathological evolution or resolution of the inflammatory response in the lung must be open to question.

The role of fibrin in the acute inflammatory response, considered in the light of the structural and functional vulnerability of pulmonary alveoli, it therefore can be no coincidence that the lung was first recognized to be the site of lamellar body secretion, and we now show that additional to whatever surfactant properties they provide, lamellar bodies have a profound effect on the formation and removal of extra-vascular fibrin.

Hyaline Membrane Disease

Surface active phospholipids accumulating in the lungs during late gestation, lower the surface tension of the foetal pulmonary fluid and reduce the resistance to aeration due to capillarity in the finer airways. Thus an adequate amount of pulmonary surfactant secreted as lamellar bodies must be present at birth for the initiation and maintenance of respiration.

Neonatal surfactant deficiency gives rise to a condition variously known as Respiratory Distress Syndrome or Hyaline Membrane Disease. Its commonest cause is prematurity, where Type II pneumocytes in the immature lung fail to secrete a sufficiency of surfactant to establish normal physiological conditions for maintenance of respiration. The basic biological concept which totally dominates our understanding of the pathophysiology of this syndrome and which is solely responsible for the only therapeutic strategy, is the role of surfactant in establishing adequate gaseous exchange between alveoli and pulmonary capillaries. No other role for the presence of phospholipid bilayers in pulmonary alveoli is recognized. Thus all pharmaceutical efforts are concentrated on providing surfactant in its most complete and natural form to meet all the physical criteria and pulmonary mechanics of gaseous exchange. However, the older name of Hyaline Membrane Disease historically marks the concern by the pathologists who coined this term, over the striking histological findings in the pulmonary alveoli of neonates dying of this condition. The use of the term "membrane" indicates a physical barrier between alveolar air and the underlying blood vessels. "Hyaline membrane" was an imprecise pathological term for eosinophilic acellular material. Modern histochemistry and electron microscopy have shown that in fact, hyaline membrane consists largely of fibrin.

The applicant's research has shown that not only are lamellar bodies required for establishing the appropriate physical conditions for gaseous exchange, but that lamellar bodies are a key balancing element in modifying the deposition and removal of fibrin. Thus synthetic or natural lamellar bodies will be used and applied to the respiratory passages and alveoli of neonates to obtain dissolution of the hyaline membrane (fibrin) as a key part of a dual therapy, along with surfactants containing spreading factors for establishment of adequate gaseous exchange.

Current mortality, despite the use of surfactant, is due to the fact that these preparations do not supply a sufficient density of phospholipids as lamellar bodies to lyse and fragment the fibrin membrane which, if unremoved, completely negates any administration of surface active phospholipids with spreading factors.

Use of Lamellar Bodies in Peritoneal Dialysis

Exudation of fibrin from the peritoneum frequently occurs in peritoneal dialysis in response to a wide variety of stimuli which provoke an inflammatory response. These include bacterial and fungal infections, endotoxin, antiseptics used in exchange procedures, which have entered the dialysate pathway, pharmacological agents added to dialysate eg, antibiotics. As a novel form of treatment to prevent the recognized pathological sequelae which may result in the abandonment of this life-maintaining therapy, intraperitoneal infusion of a solution containing a high concentration of synthetic lamellar bodies can be used to dissolve formed fibrin and modify forming fibrin, to prevent the genesis of peritoneal fibrosis and the formation of intra-abdominal adhesions, omental adhesions to peritoneal catheter, and catheter blockage.

When a patient is being removed from peritoneal dialysis, solutions of synthetic lamellar bodies should be infused per catheter into the peritoneum after cessation of dialysis. This is to prevent adhesions forming between areas of peritoneal surface which have been denuded of mesothelial cell cover.

Sclerosing peritonitis, a rare but serious complication of peritoneal dialysis, where global loss of mesothelium leading to loss of intraperitoneal production of lamellar bodies and global fibrin exudation results in widespread adhesions which cannot be relieved by surgical intervention. This usually fatal complication should now be treated by per catheter infusions of solutions of synthetic lamellar bodies into the peritoneum. At the onset of this condition the patient should receive continuous dialysis in which the dialysate contains a titrated amount of synthetic lamellar bodies. If widespread surgical adhesiolysis is to be carried out, exposure to solutions of synthetic lamellar bodies should begin intra-operatively and be continued under regular abdominal ultrasonic monitoring until a mesothelial cell layer regenerates from stem cells to cover the raw, dissected surfaces of visceral and parietal peritoneum, for a period which should range from twelve to twenty days.

Production of Synthetic Lamellar Bodies

One method for preparing the synthetic lamellar bodies of the present application is shown below.

Phospholipid multilamellar microbodies are constructed using specific phospholipids in proportions similar to those found in lamellar bodies in normal tissues. The key feature that distinguishes the phospholipid multilamellar microbodies described in the present application from liposomes is their low content or absence of cholesterol. In biomedical applications liposomes, as synthetic constructs, are primarily designed for compartmental containment and preservation of pharmaceuticals and diverse agents. Thus they are constructed with high levels of cholesterol which confer a membrane stability and low porosity, mimicking mammalian cell membranes. Therefore it follows that the bilayer concentration of cholesterol is the key determinant of the circulatory half-life for liposomes designed as drug carriers. The inhibitory effect of cholesterol on the up-take of liposomes by the lympho-reticular system, as measured in liver and spleen, is well-established. In direct contrast, phospholipid multilamellar microbodies, modelled on the properties of lamellar bodies, are readily taken up by phagocytic cells and as in the case of liposomes with low cholesterol content, are rapidly removed from circulation by lympho-reticular tissue.

The principle phospholipid constituents of lamellar bodies are phosphatidylcholine (PC), sphingomyelin (SPH), phosphatidylethanolamine (PE), phosphatidylserine (PS), phosphatidylinositol (PI) and lysolecithin (LPC). The phospholipid composition of lamellar bodies shows slight variation according to the cell of origin.

PC is the principle phospholipid in lamellar bodies, irrespective of site of origin. The percentage PC concentration varies from around 70% in lung lavage to 45% in synovial fluid. The next phospholipid in ranking concentration is SPH (5-15%). Thereafter, PE, PS, PI, PG and LPC are present in varying, single digit percentage concentrations in lamellar bodies according to site of origin.

The preferred composition of phospholipids and cholesterol for phospholipid multilamellar microbodies comprises: PC 54%: SPH 19%: PE 8%: PS 4%: PI 3%: cholesterol 10%. These values are median and the following range of compositions have been found in natural lamellar bodies: PC 44-60%, SPH 15-23%, PE 6-10%, PS 2-6%, PI 2-4%, Cholesterol 4-12%. These figures are percentage by weight.

LPC may also be incorporated into the multilamellar microbodies at 2% by weight which follows the range found in natural lamellar bodies of 0-3%.

Phospholipid vesicles in the form of liposomes are, of course, well known. However, liposomes are made by those skilled in the art with high cholesterol concentrations to improve their rigidity. Liposomes containing cholesterol at 20% or below would be considered to be cholesterol poor. Liposomes incorporating a high ratio (50%) of cholesterol, where it is equimolar with the phospholipids, have a highly stable structure and so, until this invention, it would not to our knowledge have been obvious to try using low-cholesterol multilamellar microbodies. The cholesterol content of lamellar bodies derived from pulmonary alveoli has been found to contain around 10% cholesterol (Schmitz G, Muller J 1991 J Lipid Research. 32:1539).

The presence of sphingomyelin in natural lamellar bodies and in the phospholipid multilamellar microbodies claimed in the present invention is important. Sphingomyelin is not generally used, to our knowledge, in liposomes and serves to give flexibility and softness to lamellar bodies. Conventional liposome technology teaches that rigidity is better for the delivery of chemicals; however, we have found that flexible, low-cholesterol, sphingomyelin containing phospholipid multilamellar microbodies are ideal for delivery of antigen to antigen presenting cells.

Phospholipid multilamellar microbodies (synthetic lamellar bodies) are prepared by a technique similar to that used to produce hand-shaken multi-lamellar vesicles (New RRC, 1990 Liposomes: A Practical Approach Oxford University Press New york PP36-39). The phospholipid mixture, together with cholesterol in the percentages given by weight are dissolved in a chloroform/methanol solvent mixture (2:1 vol/vol). The lipid solution is introduced into a round-bottomed flask and attached to a rotary evaporator. The flask is evacuated and rotated at 60 r.p.m. in a thermostatically controlled waterbath at a temperature of 30° C. until a dry lipid film is deposited. Nitrogen is introduced into the flask and the residual solvent is removed before its connection to a lyophilizer where it is subjected to a high vacuum at room temperature for one hour. After release of the vacuum and following flushing with nitrogen, saline containing solutes (selected antigen) for entrapment is added. The lipid is hydrated within the flask, flushed with nitrogen, attached to the evaporator, and rotated at 60 r.p.m. at room temperature for thirty minutes. The suspension is allowed to stand for two hours at room temperature to complete the swelling process.

It can therefore be seen that there are many uses for lamellar body solutions in surgical procedures. It should also be noted that the embodiments disclosed above are merely exemplary of the invention, which may be embodied in many different forms. Therefore, details disclosed herein are not to be interpreted as limiting, but merely as a basis for claims and for teaching one skilled in the art as to the various uses of the present invention in any appropriate manner.

Pharmaceutical Compositions and Methods of Delivery

Another aspect of the invention provides for pharmaceutical compositions comprising purified lamellar bodies or microbodies which act as surrogate lamellar bodies in body cavities, blood vessels, ducts and tissues to modify the deposition and removal of extra and intra-vascular fibrin for therapeutic purposes. In addition, the invention relates to pharmaceutical compositions containing synthetic or naturally occurring lamellar bodies for preventing post-operative adhesions by administration of, or treating patients having adhesions or at risk for getting adhesions resulting from a surgical procedure.

One embodiment features treatment of a wide range of surgical procedures with pharmaceutical compositions containing synthetic or naturally occurring lamellar bodies or microbodies and acceptable carriers and excipients. Moreover, a further embodiment may include a pharmaceutical composition designed for use in local treatment of adhesions. Another embodiment may include a pharmaceutical composition designed for systemic use alone or with other standard treatment modalities known to those skilled in the art.

Such compositions comprise a therapeutically effective amount of an agent, and a pharmaceutically acceptable carrier. In a particular embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the subject. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The amount of the compound of the invention which will be effective in the treatment of the conditions described herein can be determined by standard clinical techniques based on the present description. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

In a specific embodiment, it may be desirable to administer the pharmaceutical compositions of the invention locally to the area in need of treatment; this may be achieved, for example, and not by way of limitation, by local infusion during surgery or by spraying the solution containing the lamellar bodies onto the exposed tissue following surgery, by topical application, by injection, by means of a catheter, or by means of an implant, said implant being of a porous, non-porous, or gelatinous material, including membranes, such as sialastic membranes, or fibers or co-polymers such as Elvax (see Ruan et al, 1992, Proc Natl Acad Sci USA, 89:10872-10876). In one embodiment, administration can be by direct injection by aerosol inhaler.

In yet another embodiment, the lamellar bodies can be delivered in a controlled release system. In one embodiment, a pump may be used (see Langer, supra; Sefton (1987) CRC Crit. Ref. Biomed. Eng. 14:201; Buchwald et al. (1980) Surgery 88:507; Saudek et al. (1989) N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. (1983) Macromol. Sci. Rev. Macromol. Chem. 23:61; see also Levy et al. (1985) Science 228:190; During et al. (1989) Ann. Neurol. 25:351; Howard et al. (1989) J. Neurosurg. 71:105). In yet another embodiment, a controlled release system can be placed in proximity of the therapeutic target, thus requiring only a fraction of the systemic dose (see, e.g., Goodson, in Medical Applications of Controlled Release (1984) supra, vol. 2, pp. 115-138). Other suitable controlled release systems are discussed in the review by Langer (1990) Science 249:1527-1533.

EXAMPLES

Example 1

Effect of Surrogate Lamellar Bodies on Fibrin Gelation in In Vitro Models

Synthetic lamellar bodies were made using a mixture of phospholipids—phosphatidylcholine, sphingomyelin, phosphatidylserine, phosphatidylethanolamine, phosphatidylinositol and cholesterol in 0.9% sodium chloride. The size range of the synthetic lamellar bodies and the ultrastructural configuration of the lamellar bilayers were shown by transmission electron microscopy to be congruent with naturally occurring lamellar bodies. The synthetic lamellar bodies were also tested for sterility.

Fibrin clots were formed using human fibrinogen and human thrombin. The fibrinogen at 2 mg per ml and thrombin at a final concentration of 0.05 µg per ml were aloquotted on a 0.5M tris-HCl buffer+0.1M sodium chloride+0.018M calcium chloride. To 200 µL of fibrinogen solution, 25 µL of thrombin was added, mixed and allowed to clot for 60 minutes. The formed clot was then overlain with 200 µL of buffer and incubated for one hour at 37° C.

Fibrin gelation is influenced by the ionic strength of solution. Thus, the dilution effect of adding synthetic lamellar bodies made in 0.9% sodium chloride was compensated by appropriate adjustments in fibrinogen and thrombin concentrations. The effect of changes to the salt balance and clot formation and structure was also independently analyzed and characterized. Clots formed with and without synthetic lamellar bodies were initially made in specially adapted cryovials to facilitate easy clot removal. Subsequent clots made for different studies were formed in 2 ml syringes, 48 microtiter plates and semimicro plastic cuvettes.

Example 2

The Gross Characteristics of Standard Fibrin Clots and Clots Formed in the Presence of Synthetic Lamellar Bodies Fibrin clots formed in the in vitro model were white in colour with a variable translucency. Synthetic lamellar body containing clots were also visibly more translucent than standard clots. They did not adhere to plastic and glass surfaces in contrast to standard clots which were strongly adherent to plastic and glass surfaces.

The difference between clots formed under standard conditions and those formed by adding increasing concentrations of synthetic lamellar body is directly related to the porosity of the clot. In turn, clot density is a function of the degree of separation of the fibrin fibers, which is dependent on the concentration of synthetic lamellar bodies present at the onset of gelation.

The three dimensional structure of the gel reflecting its density can be accurately measured and expressed in three modes:
1. ultrastructure of fibrin network by transmission and scanning electron microscopy;
2. absorbence of transmitted light at 620 Å; and
3. impedance of fluid passage through the gel.

Time course studies of the dynamic process of gelation were investigated using all three methods of measurement. These showed that addition of even small amounts of synthetic lamellar bodies significantly altered the time course of polymerization of fibrinogen to fibrin.

Example 3

Ultrastructural Morphology of Standard Fibrin Clots and Clots Formed with Synthetic Lamellar Bodies The morphology of clots formed with different concentrations of synthetic lamellar bodies, when compared to that of standard clots, provided considerable insight into the effect of synthetic lamellar bodies on gelation. Clots examined by transmission and scanning electron microscopy were fixed in 2.5% glutaraldehyde, 2% tannic acid mixture and post-fixed in 1% osmium tetroxide in order to preserve the synthetic lamellar bodies.

On scanning electron microscopy, standard clots showed a dense network of branching and interlaced solid fibers of fibrin. Additionally, numerous small nodules were regularly distributed throughout the fibers. The three dimensional ultrastructural appearances, relative thickness and separation of the fibers, together with nodules, were closely similar to those encountered in the many peritoneal biopsies of human peritoneum exhibiting freshly deposited fibrin. The in vitro clots and the peritoneal biopsies were fixed and processed in identical fashion. Thus, the close ultrastructural concordance between in vitro fibrin clot formation and in vivo peritoneal extravascular fibrin formation gives considerable credence to and hence confidence in the results of information derived from the in vitro model. The peritoneal biopsies were obtained by the International Peritoneal Biopsy Registry from over a thousand patient samples.

Transmission electron microscopy of standard fibrin clots showed moderately osmophilic, fine fibrils arranged in bundles separated from each other by regular clear spaces. Again, the ultrastructural appearances were closely similar to those seen in vivo in peritoneal biopsies from patients before, during and after peritoneal dialysis and from patients undergoing routine abdominal surgery.

Scanning electron microscopy of fibrin clots formed with different concentrations of synthetic lamellar bodies showed significantly different three dimensional architecture from that seen in standard fibrin clots. Fibrin fibers were coarser, irregular and ragged as compared with those seen in standard clots. Spaces within the network were greater due to wider separation of fibers.

Transmission electron micrographs of fibrin clots formed with synthetic lamellar bodies displayed a radically different ultrastructural appearance to that encountered in standard clots. Whereas in standard clots the geometry was exclusively one of fibrin fibers arranged in a rectilinear network, in clots formed with synthetic lamellar bodies, the fibers showed additional geometric configurations which were curvilinear or circular, reflecting the vesicular nature of the synthetic lamellar bodies. As shown by scanning electron microscopy, the network was looser due to widening of spaces between fibers.

Example 4

Absorbance of Transmitted Light at 620 Å

The two reactants, fibrinogen and thrombin, are soluble in electrolyte solution to give a clear fluid with only minimal absorbence of light. The dynamic process of polymerization confers an opacity or turbidity which increases with time up to a limit. This process can be accurately recorded in a spectrophotometer by measuring absorbance of light at 620 Å. In standard fibrin clots there is a rapid development of turbidity which reaches a maximum within a relatively short period. Synthetic lamellar bodies possess low turbidity as do natural lamellar bodies. Addition of synthetic lamellar bodies at the same time as the mixing of thrombin and fibrinogen produces a clot which shows a significantly different pattern of light absorbance to that seen in the process of standard clot formation. The turbidity develops more slowly, and after plateauing at a maximum, lower than that seen in the standard fibrin clot, the turbidity falls back to base levels over a 24 hour period. The observations on turbidity indicate that synthetic lamellar bodies grossly alter the process of clot formation, both chronologically and structurally, reflecting alteration in the rate and manner of polymerization of fibrinogen to fibrin. This shows that incorporation of synthetic lamellar bodies into a forming clot results in its dissolution after 24 hours to 5 days, dependant on the volume and concentration of synthetic lamellar bodies and the volume of the clot.

Example 5

Impedance of Fluid Passage Through Standard Fibrin Clots and Clots Formed with Synthetic Lamellar Bodies Comparison of the rates of flow of a fluid through gel networks is a measurement of relative pore size in the test of material. A simple experiment carried out using a standard fibrin clot and a fibrin clot containing synthetic lamellar bodies can be formed in a 2 ml syringe. A Whatman filter paper was placed over the base of the syringe to cover the aperture. At a fixed pressure, the rate of passage of buffer through the syringe can be measured. This shows that the passage of fluid through a synthetic lamellar body-containing clot is at least 30% faster than in the standard fibrin clot, indicating a significantly greater pore size in clots formed in the presence of synthetic lamellar bodies.

Example 6

Effect of Addition of a Saline Solution Containing Synthetic Lamellar Bodies to Pre-formed Standard Fibrin Clots Using the same concentrations of synthetic lamellar bodies as were incorporated in actively forming fibrin clots, experiments were carried out where synthetic lamellar body solutions were overlain at different time intervals to pre-formed standard fibrin clots. It was found that at room temperature and at 37° C. application of synthetic lamellar bodies resulted in dissolution of the clot by 24 hours to 5 days, dependant on the volume and concentration of synthetic lamellar bodies and the volume of the clot. Fibrin clots in an in vitro system using only thrombin possessed relatively weak non-covalent lateral bonding between fibers. For a stable fibrin network Factor 13 (fibrin stabilizing factor), a transamidase is required to effect lateral bonding through the formation of peptide linkages.

Example 7

Effect of Addition of a Saline Solution Containing Synthetic Lamellar Bodies on a Pre-formed Human Whole Blood Clot Freshly collected venous human blood is collected and allowed to clot in tubes. After one hour, when clot retraction has occurred, the serum is decanted and a saline solution containing synthetic lamellar bodies is added. After 24 hours to 5 days, dependant on the volume and concentration of synthetic lamellar bodies and the volume of the clot, the clot is completely dissolved. Clots aged in buffer at 37° C. for 24 hours to 5 days also show a similar degree of dissolution following after 24 hours to 5 days exposure to synthetic lamellar body containing solutions.

Example 8

Mode of Action of Synthetic Lamellar Bodies in Fibrin Formation and Fragmentation Lamellar bodies represent a unique agent for influencing the polymerization of fibrinogen to fibrin during the active process, and also influencing the fragmentation of pre-formed fibrin. Their action in this respect is unique, as they are not proteolytic enzymes. Synthetic lamellar bodies, as surrogate lamellar bodies, are microbodies 0.3 to 3.5μ in diameter, in contrast to globular protein molecules which are the predominant players in the coagulant and fibrinolytic cascades.

Investigations carried out by the inventor indicate that part of the mode of action of synthetic lamellar bodies is to sequester factors involved in coagulation by attachment to the phospholipid bilayers. Since synthetic lamellar bodies are multilamellar and highly deformable, they can form and reform when in contact with each other. This property of exposing a constantly changing surface layer confers synthetic lamellar bodies with a massive capacity to adsorb and entrap factors crucial to the coagulant cascade.

As mentioned previously, the fibrinogen molecule is an asymmetric rod-shaped dimer which, upon activation, polymerizes by end-to-end and side-to-side association, forming protofibrils. The protofibrils associate to form fibrin fibers and the latter join into bundles of larger widths. The protofibrils are twisted in a helical fashion. The fibrin fibers are also twisted. Helical twisting determines the absolute diameter of the fibrin fibers, in that accretion of fibers stops when the torque of the outer fibers increases to the point that the amount and energy necessary to the stretch the outer protofibrils exceeds the energy available for bonding. The innate twisting of fibrin fibers sets a limit on the lateral aggregation and hence radial growth. Fibrin fibers are known to conform to a three dimensional rectilinear geometry in the fibrin network. Although both protofibrils and fibers are twisted to confer maximum strength, the fibers themselves are not curved but rectilinear. When looking at pure fibrin clots, the size and plasticity of the synthetic lamellar bodies allow them to percolate through and between the fibrin threads in the developing reticulum. The spherical presence within a developing rectilinear fibrin network will impose abnormal structural strain on the fibrils whose self-assembly in polymerization is dependent on helical twisting. Therefore, fibers forming around curvilinear microbodies will be subjected to an additional mechanical strain where bending of the fibers will create a higher energy level in the protofibrils on the outer aspect of the convexity and overcome the bonding energy between the protofibrils. This will result in fibers of significantly reduced size through the imposition of a new lower limit on the radial diameter of the fibers. Thus, the presence of synthetic lamellar bodies within a developing clot will introduce a mechanical strain restricting the formation of self-sustaining, self-propagating fibrin networks.

What is claimed is:

1. A method of treating adhesions comprising administering a therapeutically effective amount of a composition comprising lamellar bodies, wherein said lamellar bodies comprise about 44-60% phosphatidylcholine, about 15-23% sphingomyelin, about 6-10% phosphatidyl ethanolamine, about 2-6% phosphatidyl serine, about 2-4% phosphatidyl inositol and about 4-12% cholesterol by weight, and a pharmaceutically acceptable carrier.

2. The method of claim 1, wherein said composition further comprises up to about 3% by weight of lysophosphatidyl choline.

3. The method of claim 1 wherein said lamellar bodies comprise about 54% phosphatidylcholine, about 19% sphingomyelin, about 8% phosphatidyl ethanolamine, about 4% phosphatidyl serine, about 3% phosphatidyl inositol and about 10% cholesterol by weight, and a pharmaceutically acceptable carrier.

4. The method of claim 1, wherein said composition further comprises about 2% by weight of lysophosphatidyl choline.

5. The method of claim 1, wherein said composition is prepared as a solution.

6. The method of claim 5, wherein said composition further comprises a combination with hyaluronan and/or chondroitin sulphate B.

7. A method according to claim 1, wherein said composition is used in combination with hyaluronan and/or chondroitin sulphate B.

8. A method according to claim 1, wherein said composition is administered at 30 minute intervals.

9. The method of claim 5, wherein said lamellar bodies are present in a concentration of about $10 \times 10^9$/ml.

10. The method of claim 1, wherein said lamellar bodies incorporate at least one other therapeutically active agent.

11. The method of claim 10, wherein said other therapeutically active agent comprises at least one anti-estrogen compound.

12. The method of claim 10, wherein said other therapeutically active agent comprises at least one chemotherapeutic anti-tumor compound.

13. The method of claim 1, wherein said administering occurs during surgical procedures.

14. The method of claim 1, wherein said administering comprises spraying the area to be treated.

* * * * *

UNITED STATES PATENT AND TRADEMARK OFFICE
CERTIFICATE OF CORRECTION

| | | |
|---|---|---|
| PATENT NO. | : 7,906,139 B2 | Page 1 of 1 |
| APPLICATION NO. | : 10/678743 | |
| DATED | : March 15, 2011 | |
| INVENTOR(S) | : James Dobbie | |

It is certified that error appears in the above-identified patent and that said Letters Patent is hereby corrected as shown below:

Title Page item [63]

Related U.S. Application Data:

Should read

Continuation-in-Part of application No. PCT/GB03/01451, filed on April 2, 2003 which claims priority to GB 0207653.7, filed on April 3, 2002.

Signed and Sealed this
Fifth Day of July, 2011

David J. Kappos
*Director of the United States Patent and Trademark Office*